US007056733B2

(12) United States Patent
Howe

(10) Patent No.: US 7,056,733 B2
(45) Date of Patent: Jun. 6, 2006

(54) **NUCLEIC ACIDS ENCODING *SARCOCYSTIS NEURONA* ANTIGEN AND USES THEREOF**

(75) Inventor: Daniel K. Howe, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/369,430

(22) Filed: Feb. 19, 2003

(65) Prior Publication Data

US 2004/0162418 A1    Aug. 19, 2004

(51) Int. Cl.
*C12N 15/00* (2006.01)

(52) U.S. Cl. ................. 435/320.1; 536/23.7; 536/24.1; 536/24.2; 536/24.32

(58) Field of Classification Search ............. 435/320.1; 536/23.7, 24.1, 24.2, 24.32
See application file for complete search history.

(56) References Cited

U.S. PATENT DOCUMENTS

| 5,670,367 A | * | 9/1997 | Dorner et al. ........... 435/320.1 |
| 2002/0115828 A1 | | 8/2002 | Dame et al. | |

OTHER PUBLICATIONS

Eschenbacher K-H et al. "Cloning and expression in *Escherichia coli* of cDNAs encoding a 31-kilodalton surface antigen of *Sarcocystis muris*", Molec, Biochem. Parasitol 1992,53:159-168.
Velge-Roussel F et al., "Intranasal Immunization with *Toxoplasma gondii* SAG1 induces protective cells into both NALT and GALT compartments", Infections and Immuniyt, 2000,68:969-972.
Nielsen H.V et al. "Complete protectin against lethal *Toxoplasma gondii* infection in mice immunized with a plasmid encoding the SAG1 gene" Infection and Immuniyt, 1999, 67:6358-6363.
Petersen E, Nielsen HV, Christiansen L, Spenter J, "Immunization with E.Coli produced recombinant T.Gondii SAG1 with alum as adjuvant protect mice against lethal infection wiht *Toxoplasma gondii*" Vaccine. Aug. 1998;16(13):1283-9.
Bonefant C, Dimier-Poisson I, Velge-Roussel F, Buzoni-Gatel D, Del Guidice G, Tappouli R, Bout D, "Intranasal immunizations with SAG1 and nontoxic mutant heat-labile entertoxins protects mice against *Toxoplasma gondii*"Infect Immun. Mar. 2001; 68(9):4948-53.
Haumont M. Delhaye L, Garcia L, Jurado M, Mazzu P, Daminet V, Verlant V, Bollen A, Beaumans R, Jacquet A., "Protective immunity against congenital toxoplasmosis with recombinant SAG1 protein in a guniea pig model", Infect Immun. Sep. 2000, '68(9):4948-53.
Angus CW, Klivington-Evans D, Dubey JP, Kovacs JA. "Immunization with a DNA plasmid encoding the SAG1(P30) protein of *Toxoplasma gondii* is immunogenic and protective in rodents" J.Infect Dis Jan. 2000;181(1):317-24.
Fort Dodge Animal Health, "Vaccine Development" brochure- 14 pages, Fort Dodge Animal Health 2001.
Fort Dodge Animal Helath advetisement for *Sarcocystis neurona* Vaccine, 3 pages, Fort Dodge Animal Health 2001.

* cited by examiner

*Primary Examiner*—Jennifer E. Graser
(74) *Attorney, Agent, or Firm*—King & Schickli, PLLC

(57) ABSTRACT

The present invention provides novel isolated nucleic acids encoding antigenic proteins derived from *Sarcocystis neurona*, or unique fragments thereof. In particular, the invention provides novel isolated nucleic acids encoding membrane-associated polypeptides SnSAG2, SnSAG3, and SnSAG4. Also provided are purified antigenic polypeptide fragments encoded by the novel nucleic acid sequences set forth herein that encode for SnSAG2, SnSAG3, and SnSAG4. Also provided are isolated nucleic acids capable of selectively hybridizing with the nucleic acid from *Sarcocystis neurona*. The invention also provides vectors comprising the nucleic acids of the invention encoding an antigenic protein derived from *Sarcocystis neurona* or a unique fragment thereof and provides the vector in a host capable of expressing the polypeptide encoded by that nucleic acid.

16 Claims, 5 Drawing Sheets

Fig. 1

```
            1        10         20         30         40         50         60         70        80
            |--------+----------+----------+----------+----------+----------+----------+---------|
SnSAG2                                   QVAT--IFC QAG--MTP-VSLG-PGQS-FYLN CRPFTIATPANFHT---NAC AG-TGAN CNPE-TYAKLFPK
TgSAG1                                   SDPPLVANQVVYC DKK--STARVILT-PTENHFTLK CKTALTEPPTLAYSPNRQ CAG-TTSQ C SKAVTLSSLIPE
TgSRS2                                   GPPYRYEPEKF C PKKGILSQAVSLLYQVQHNITFA CEATPYPTLISEEHGLMV CENMTPEB CANPAPLSAFLPG
Consensus                                ..p..va.....tC..kk...t...VsL..p.#..ft1.C............tp.........C.....ag.T...C.....tls.l.p.

81        90        100        110        120        130        140        150       160
            |--------+----------+----------+----------+----------+----------+----------+---------|
SnSAG2      ASNHVVVSPADST-SATHTWTAPAANQLSGKTYFSVQC STGDPAGI CNYDVTYSS
TgSAG1      AEDSWATGDSASLDTAGIKLTVPIEKFPVTTQTFYVQ CIK-GDDAQ CHVTVTVQARASSYVNNYARCSYGANSTLGPYK
TgSRS2      ATKEHVTGDSVLT---GLKISVPESQYPANAKSFRVQ CHNTKTGNT CNLTIHVEPRDPAVERQEARCSYTENSTLPKIF
Consensus   A...wwtgds.st...ag.k.tvP.....F.VQC........gd.a..Cnvtitv..r....v....arcsy..nstl....

161       170        180        190        200        210        220        230       240
            |--------+----------+----------+----------+----------+----------+----------+---------|
SnSAG2      LSAEGPTTHTLVCGKDGVKVPQDDNQ-YCSGTTLTGCNEKSFKDILPKLSENPAQGNASSDNGATLTINKEAFPAESKSV
TgSAG1      VTKDS-WTHTLRCGPHGAPMPESYTENYCS--TPDT-CDEKPFTSVIPGYLSKWFFGDPKSPLGARVRIPPEQIPSSPQIN
TgSRS2
Consensus   ........tntl.cg...g....P.......ycs.t..t.c.ek.f.....p.........g....s..ga...i..e..p......

241       250        260        270        280        290        30B02
            |--------+----------+----------+----------+----------+----------|
SnSAG2      IIGCTG----GSPEKHHCTVQLEFAGAARGSAKS
TgSAG1
TgSRS2      YFGCTGPTEGEGPKYNCTVPVPLGGGDPSEGSRPGGGSGGGGKRGGGQGGGSLAGFBFRQGS
Consensus   ..gctg....g....k....ctv........g.....s....s.......................
```

*Fig. 2*

SEQUENCE LISTING

<160> NUMBER OF SEQ ID NOS: 30

<210> SEQ ID NO 1
<211> LENGTH: 1148
<212> TYPE: DNA
<213> ORGANISM: Sarcocystis neurona

<400> SEQUENCE: 1

```
gtgccacaat gccacacaga gcagtcattt tgacatcctc tggaaacctc cctttgcaac      60
tgactggtga acaacgttgt cagcctttcg ctcctctcac gtcaggatga agcggcgttg     120
caacttccga aaagaattag tttccttttt ctggctgttc gtgctgctag gcgcggccaa     180
cgtgtttggg atttacgcgg acgatgagtg ccagcccctg ttggaacacg cagatgatga     240
cacgccaccc gaaacccta taaggccgga gagaccagtg tcgctgtctg ggtttctcca      300
caaactacta cagcgtggac gtgaacacag gccgaagtct cccgcaagcc gtacggcacg     360
gatgggaagg cagagcgacg acgccaagca aaggcgagca ggggtacttt acacaaacct     420
acttgactac gtgttcgaag cccctgaggt ggaacctaag accacgttct ggggcggcgt     480
taaacagctg cctgctggga gcgtggcgat gactggtttc acgatgttgc ctagatagta     540
cccgccgatg gttggaaaag ttggtcaggt cctgcctgaa acatacacag ccgcgtttgg     600
cgggggttat attgccgtga caggcgacag gagtacagac aatgattata tccctctgcg     660
gactgtcaat tcaaactaac tgctgcgtct cctgcgcctt agccgccttt gttcagccca     720
tatagccggc ggtcctcttt ctttcgtaat gcatgggggac tgctgtgaac aagaaggaag     780
acggaggcaa tggggactag gccgccaaca ctagttgagg cactggaact gtgtgcgtgt     840
```

-continued

```
ctttgttgtt gctgctttca cctgcatggt tgcacgttac agacgggtga ggctcaccta    900
gaacaaggga tcctgcccgc cgcgggtgag tgccggtggg tccaatttta agcgcgcgta    960
gaatgccacg cgttgggctt ggcagatgag acaacaaagt gtggtgacaa atttgcgatc   1020
cgttgcagac cggtagaggc gtagagacga caacctgctc ttgtgctgga aaacagttat   1080
tctgaaagaa ttttctaatg aacagcggct cggcacggtc cgccgaaaac ccgggtgtag   1140
tggtggtc                                                            1148

<210> SEQ ID NO 2
<211> LENGTH: 143
<212> TYPE: PRT
<213> ORGANISM: Sarcocystis neurona

<400> SEQUENCE: 2

Met Lys Arg Arg Cys Asn Phe Arg Lys Glu Leu Val Ser Phe Phe Trp
1               5                   10                  15

Leu Phe Val Leu Leu Gly Ala Ala Asn Val Phe Gly Ile Tyr Ala Asp
            20                  25                  30

Asp Glu Cys Gln Pro Leu Leu Glu His Ala Asp Asp Asp Thr Pro Pro
        35                  40                  45

Glu Thr Pro Ile Arg Pro Glu Arg Pro Val Ser Leu Ser Gly Phe Leu
    50                  55                  60

His Lys Leu Leu Gln Arg Gly Arg Glu His Arg Pro Lys Ser Pro Ala
65                  70                  75                  80

Ser Arg Thr Ala Arg Met Gly Arg Gln Ser Asp Asp Ala Lys Gln Arg
                85                  90                  95

Arg Ala Gly Val Leu Tyr Thr Asn Leu Leu Asp Tyr Val Phe Glu Ala
            100                 105                 110

Pro Glu Val Glu Pro Lys Thr Thr Phe Trp Gly Gly Val Lys Gln Leu
        115                 120                 125

Pro Ala Gly Ser Val Ala Met Thr Gly Phe Thr Met Leu Pro Arg
    130                 135                 140

<210> SEQ ID NO 3
<211> LENGTH: 1393
<212> TYPE: DNA
<213> ORGANISM: Sarcocystis neurona

<400> SEQUENCE: 3
agtattttcc cgcgtttttg agagaccaca ctgtgcttcg tttacagtta tgctgaatgt     60
cgcgcagctg ccgcattgtt cggtcgttcg tcagttagca cctattctgg taacgtaacc    120
gcgattacgt atcgcatcaa ctttatcccg attccgtggt ggatgctctt ggcacgtggc    180
ccgcgtccgt agtcggggac gcacgtcttt ttccgtgtcg ttcgtcgtgt tttccctcta    240
catgcgtcaa gactcgccac taagcgcgcc acgagcctca tccgtgaaca actcgaaatg    300
gggaaggcgg tgacaggact tttcctttgc gtgacgctcc ttatttgctg ccgccctgtc    360
agcagcagtg tttttactta caaccacctc gtccggagta tatttcgaat gcctgacgtg    420
caacacaacc agcagctagc tcagctagcg gcaaggtgcc tgcaagaagt aaaacgcgct    480
ggccatgagg acgacatcga ggctgcctta gctagtgacg ctgtcgtcaa gtgtcttagt    540
gatttctcgg ttgcgcacgc gcagatgctt ctaccacttc gaaaggatcc ggaaacaatt    600
gcagctctaa agggggccat agcccttgct tcacaagagg actttgctga ggttatccgg    660
gatcgagttc gacgcgatac gtttgtaacg gcctattacg cggacaccga cataaatctg    720
```

-continued

```
gcgagcccat cgggcaagct tacgtaaatc tggcgagccc attggacaat tctacgaatg      780
ggtggagtgt aaaaaccggt ctgttccttt tatgttacgt gctgtggaca gcgaggtaag      840
gcgtcggtcc gccctagtcc aaagtaaatc atgcaaaagc attcgagaaa tggggaggat      900
gccatgctcc ccatttgggg tgataaatca ccgtttcttt acgggagggc agacaagtag      960
aaggttacgt ttgtactacc tgaacaacga agttactgcg gcttgcagga acggactttg     1020
ctggaaccga cagacggcgc aggaatgcgc ctggtgtttc aactgaaagc agcctccccg     1080
ttaagtgtat gcctgcgaaa tccccacccg gtatcgtgtc atccgcatgt tgtctttgag     1140
cgcgtgagtt gggtgttcat gatgttgggt ctgtcggggt tgacgtttcc tccgtgtgta     1200
cttttataat attgcggcgt ggtgtcgtgt tataaacgct ttgacttctt tggcttacgt     1260
atggtgaatg ttgtgcgaga gagccacgaa ggaatgacac gctggcgcag acatagtact     1320
gtgcgtttcc acttttcaca ctgtggcatt tatgcttctt ccaatgatgc cgaacgtctg     1380
agccacacct ggg                                                        1393
```

<210> SEQ ID NO 4
<211> LENGTH: 149
<212> TYPE: PRT
<213> ORGANISM: Sarcocystis neurona

<400> SEQUENCE: 4

```
Met Gly Lys Ala Val Thr Gly Leu Phe Leu Cys Val Thr Leu Leu Ile
1               5                   10                  15

Cys Cys Arg Pro Val Ser Ser Val Phe Thr Tyr Asn His Leu Val
            20                  25                  30

Arg Ser Ile Phe Arg Met Pro Asp Val Gln His Asn Gln Gln Leu Ala
        35                  40                  45

Gln Leu Ala Ala Arg Cys Leu Gln Glu Val Lys Arg Ala Gly His Glu
    50                  55                  60

Asp Asp Ile Glu Ala Ala Leu Ala Ser Asp Ala Val Val Lys Cys Leu
65                  70                  75                  80

Ser Asp Phe Ser Val Ala His Ala Gln Met Leu Leu Pro Leu Arg Lys
                85                  90                  95

Asp Pro Glu Thr Ile Ala Ala Leu Lys Gly Ala Ile Ala Leu Ala Ser
            100                 105                 110

Gln Glu Asp Phe Ala Glu Val Ile Arg Asp Arg Val Arg Arg Asp Thr
        115                 120                 125

Phe Val Thr Ala Tyr Tyr Ala Asp Thr Asp Ile Asn Leu Ala Ser Pro
    130                 135                 140

Ser Gly Lys Leu Thr
145
```

<210> SEQ ID NO 5
<211> LENGTH: 973
<212> TYPE: DNA
<213> ORGANISM: Sarcocystis neurona

<400> SEQUENCE: 5

```
agagagagag agaactagtc tcgagttttg ttacttcgca ggtgcttcgc aggtgcttca       60
cattcatatt tcacttgtca ctcaactgcg gcagagtttt cagctctcga agtgcttctg      120
tgtacacaga tttgcacaat tctgttcctc ttcaactacc aacgacgttg cacagcaaaa      180
aaaccttatc aacaatgccg cgagtgtcgc tccttaatct cctggtggtg gcgacggccc      240
```

-continued

| | |
|---|---|
| ttctcgctgc tggctctacc gtcctgtgcg cggaggaaga tgtaccagga ggtacccttg | 300 |
| acacagggag ttccccggga aatccagcga gaccaccgga gaatccacta tggagccgac | 360 |
| tgactaaact cgatgcggga ccgctgacga actcattacg gaggcaactg aaaagcgctt | 420 |
| cgctcgtgtt ggcgagtctt attgctgcag cgatgttgtc gtccactaat ggaccatttg | 480 |
| tggacgcaat ggagatgaat tttacaacgc cactgtagag tcgcataact gctcgaaagg | 540 |
| agacagccaa aactagaaaa gagctctctc aaaaggctga gtacctcgtg ggcatcccac | 600 |
| aacgaaccgt gtcgacaccg tcgagttctc aagcattgag cagtgattag tcccataatt | 660 |
| gatgatcacg gccttagtat cagtttctgt atgcatacac acacgtgctg tttcgctgcg | 720 |
| ccctcactta ttgaaattgt tgtgccatcg gtgccattgt cacacctgtg tgttgctggc | 780 |
| ccctgcccac gtacacatgt aatcgtaatt cctgtatcgt cggcggtagt gtacgtagct | 840 |
| tggctgtacc ctactcgcgt aacaaatttc ctttattgtc tgtggcagtg taacgccaac | 900 |
| aagtaaatga tcagcatttt aagggatac gatacgcgct aaaaaaaaaa aaaaaaaaa | 960 |
| aaaaaaaaaa aaa | 973 |

<210> SEQ ID NO 6
<211> LENGTH: 107
<212> TYPE: PRT
<213> ORGANISM: Sarcocystis neurona

<400> SEQUENCE: 6

Met Pro Arg Val Ser Leu Leu Asn Leu Leu Val Val Ala Thr Ala Leu
1               5                   10                  15

Leu Ala Ala Gly Ser Thr Val Leu Cys Ala Glu Glu Asp Val Pro Gly
            20                  25                  30

Gly Thr Leu Asp Thr Gly Ser Ser Pro Gly Asn Pro Ala Arg Pro Pro
        35                  40                  45

Glu Asn Pro Leu Trp Ser Arg Leu Thr Lys Leu Asp Ala Gly Pro Leu
    50                  55                  60

Thr Asn Ser Leu Arg Arg Gln Leu Lys Ser Ala Ser Leu Val Leu Ala
65                  70                  75                  80

Ser Leu Ile Ala Ala Ala Met Leu Ser Ser Thr Asn Gly Pro Phe Val
                85                  90                  95

Asp Ala Met Glu Met Asn Phe Thr Thr Pro Leu
            100                 105

<210> SEQ ID NO 7
<211> LENGTH: 917
<212> TYPE: DNA
<213> ORGANISM: Sarcocystis neurona

<400> SEQUENCE: 7

| | |
|---|---|
| ctagtctcga gttttttgtt acttcgcacg tgcttcacat tcatatttca cttgtcgctc | 60 |
| aactgtggca gagttttcag ctctcgaagt gcttctgtgt acacagtttt gcacaattct | 120 |
| gttcctcttc aactgccaac gacgttgcac agcaaaaaca atcttatcaa caatgccgcg | 180 |
| actgtcgctc cttaacctcc tcttggtggc gacggccctt ctcgctgctg gttctaccgt | 240 |
| cctgtgcgcg gaggaagatg taccaggagg taaccttgac acagagagtc cgccgggaga | 300 |
| tgcaggggg ccaccggtga atccagtacg gagccgagag actgaactcg gagcgcggcc | 360 |
| gctgacgaac tcattacgga ggcaactgaa aagcgcttcg ctcgtgttgg cgagtcttat | 420 |
| tgctgcagcg atgttgtcgt ccactggtgg accatttgtg gacgcagtgg ggacgaattt | 480 |

| | |
|---|---|
| tacgtcattg tagagtcgcc taactgctcg acaggagaca gccaaaacta gaaaagagcg | 540 |
| ctctcaaaag gctgaatagg ctgatgtggg catcccacac gaaccgtgtc gacaccgagt | 600 |
| tctcaaacat tgaacagtga ttagtcccat aattgatgag gatcacggct caagacctct | 660 |
| ttctgtatgc atacaggtgc gtgttgcttc gctgagccct tacttattga aattgttgtg | 720 |
| ccatcggtgc cagtgtgaca gatgtgtgtt gcttgcctgt gcccacgtac acacggaatc | 780 |
| ggaattcctg tctcgtcggc ggtagtgtac gtagctgggc tgcgcccgta ctcgcgtaaa | 840 |
| gaattggcgt attttcgatg gcagtgtaac gtcatcgcgt aaatgactat tttaagttaa | 900 |
| aaaaaaaaaa aaaaaaa | 917 |

<210> SEQ ID NO 8
<211> LENGTH: 106
<212> TYPE: PRT
<213> ORGANISM: Sarcocystis neurona

<400> SEQUENCE: 8

Met Pro Arg Leu Ser Leu Leu Asn Leu Leu Leu Val Ala Thr Ala Leu
1               5                   10                  15

Leu Ala Ala Gly Ser Thr Val Leu Cys Ala Glu Glu Asp Val Pro Gly
            20                  25                  30

Gly Asn Leu Asp Thr Glu Ser Pro Pro Gly Asp Ala Gly Gly Pro Pro
        35                  40                  45

Val Asn Pro Val Arg Ser Arg Glu Thr Glu Leu Gly Ala Arg Pro Leu
    50                  55                  60

Thr Asn Ser Leu Arg Arg Gln Leu Lys Ser Ala Ser Leu Val Leu Ala
65                  70                  75                  80

Ser Leu Ile Ala Ala Ala Met Leu Ser Ser Thr Gly Gly Pro Phe Val
                85                  90                  95

Asp Ala Val Gly Thr Asn Phe Thr Ser Leu
            100                 105

<210> SEQ ID NO 9
<211> LENGTH: 523
<212> TYPE: DNA
<213> ORGANISM: Sarcocystis neurona

<400> SEQUENCE: 9

| | |
|---|---|
| acttcgcacg tgcttcacat tcatatttca cttgtcgctc aactgtggca gggttttcag | 60 |
| ctttcgaagt gctttctgtg tacacaaatt gcacacttc tgttgcactt caactggcaa | 120 |
| cgacgttgca cagcaaaaaa accttatcag caatgccgcg actgtcgctc cttaacctcc | 180 |
| tggtggtggc gacggccctc ctcgctgctg gctctaccgt cctgtgcgcg gaggaagatg | 240 |
| taccagactc aggtggtaac ctttacacag gaagtccgcc gggcgattca gcggggccac | 300 |
| agaaggatcc gctacggagc cgacagactg aactcggagc gcgaccgctg acgaactcat | 360 |
| tagggagaca actgaagaag ggctcgctct tgttggcgag tctcattatt gctgcagcga | 420 |
| tgttgaccga agttggggaa tttgcggatg cgtccatgca taacttcact acaactttt | 480 |
| gaagtcgcgc aaacttcaat ttcctgagag gagacagcca aaa | 523 |

<210> SEQ ID NO 10
<211> LENGTH: 109
<212> TYPE: PRT
<213> ORGANISM: Sarcocystis neurona

<400> SEQUENCE: 10

Met Pro Arg Leu Ser Leu Leu Asn Leu Leu Val Val Ala Thr Ala Leu
1               5                   10                  15

Leu Ala Ala Gly Ser Thr Val Leu Cys Ala Glu Glu Asp Val Pro Asp
            20                  25                  30

Ser Gly Gly Asn Leu Tyr Thr Gly Ser Pro Gly Asp Ser Ala Gly
                35                  40                  45

Pro Gln Lys Asp Pro Leu Arg Ser Arg Gln Thr Glu Leu Gly Ala Arg
        50                  55                  60

Pro Leu Thr Asn Ser Leu Gly Arg Gln Leu Lys Lys Gly Ser Leu Leu
65                  70                  75                  80

Leu Ala Ser Leu Ile Ile Ala Ala Ala Met Leu Thr Glu Val Gly Glu
                85                  90                  95

Phe Ala Asp Ala Ser Met His Asn Phe Thr Thr Thr Phe
            100                 105

<210> SEQ ID NO 11
<211> LENGTH: 994
<212> TYPE: DNA
<213> ORGANISM: Sarcocystis neurona

<400> SEQUENCE: 11

```
cgcacgtccg tcacattcat agttcatttg tcgctcaact gtggcagggt tttcagcttt      60
cgaaatactt tctgtgtaca caaatttgca cacttctctt caccttcaac tgacaacgac     120
gtcgcacagc aaaaaaatct tatcaacaat gccgcgcctg tcgctcctta acctcctggt     180
ggtggcgatg gccttcctcg ctgctggctc taccgtactg tgcgcggacg aagatgtaac     240
cggaggtgac gatacagcaa gcccgccgcg agattcagcg cggccaccgg agaatccact     300
acggagccga ttgacggaac tcgtagggcg acggctgatg aactcattag gaagacaagc     360
gacgaacggt tcgctcctgt tggcgagtct tctcattgct gcagcgatgc tcgtcgacat     420
gggccagtt gcgaacgcgt actcgtacaa catgacacac ccactttaat ttcttgacag     480
gaaacagaca aaaacagaaa atagctatcc tcaaaggctg aatacatcac aacggacata     540
gcaacataac ggacgcgtgg acaccgccga ggtcgcaaac gtttcacagt aattggtccg     600
ataattcatg aggattgagg ccttagtacc actttctgta tgcatataca tgattgctgc     660
tttgctgcga atcgttgtg ccatcggtgc cagtgctaca caagtgtgtt gcttgcctgc     720
gccccgtac aaacgtaatc ggaattcctg tatcctctgc ggtggtgtac gtactttcgc     780
ggtgcccgtg cccgcgtaac gaattttccg tcttctctgt tcgcggatgc tctgtgggta     840
ccagctgtgc aagagtgagc aagtgcacaa gacatcgatg aagcatagaa ctacgtcgtt     900
cgcggcaagg catacgcgct gtcactcggt tgtcgcggat gctgtgtggg taccagttgt     960
gcaaaaatta gcaagtgaaa aaaaaaaaaa aaaa                                 994
```

<210> SEQ ID NO 12
<211> LENGTH: 106
<212> TYPE: PRT
<213> ORGANISM: Sarcocystis neurona

<400> SEQUENCE: 12

Met Pro Arg Leu Ser Leu Leu Asn Leu Leu Val Val Ala Met Ala Phe
1               5                   10                  15

Leu Ala Ala Gly Ser Thr Val Leu Cys Ala Asp Glu Asp Val Thr Gly
            20                  25                  30

Gly Asp Asp Thr Ala Ser Pro Pro Arg Asp Ser Ala Arg Pro Pro Glu
            35                  40                  45

Asn Pro Leu Arg Ser Arg Leu Thr Glu Leu Val Gly Arg Arg Leu Met
        50                  55                  60

Asn Ser Leu Gly Arg Gln Ala Thr Asn Gly Ser Leu Leu Ala Ser
65                  70                  75                  80

Leu Leu Ile Ala Ala Ala Met Leu Val Asp Met Gly Pro Val Ala Asn
                85                  90                  95

Ala Tyr Ser Tyr Asn Met Thr His Pro Leu
            100                 105

<210> SEQ ID NO 13
<211> LENGTH: 822
<212> TYPE: DNA
<213> ORGANISM: Sarcocystis neurona
<220> FEATURE:
<221> NAME/KEY: misc_feature
<222> LOCATION: (746)..(746)
<223> OTHER INFORMATION: n is a, c, g, or t

<400> SEQUENCE: 13

| | | | | | |
|---|---|---|---|---|---|
| aaacggtcat | attttttgcca | gttgtcgctc | aagtgtagcg | gtcgtgcctg | cttcgcaagg | 60 |
| ccaaactgag | ttctacgtac | acaaatctgg | tcctttcgcc | ttcccctcgg | tcggcagcgt | 120 |
| tgttacgcac | cagaacagtc | acatcagcaa | tgccgcgctt | gccgctcctt | aagcacctct | 180 |
| tggtggccac | gttcctcctc | gctggtggct | ccggcgtcct | gtgcggggaa | agaggagagc | 240 |
| tcggagcaag | taaccaccgt | ggcggcggga | gtgtggatat | ccctggagct | cctcaggagt | 300 |
| cggcagtcgt | agaggatggg | acagaagcag | actcagattt | gagatttgag | gagcggctcg | 360 |
| ccctccatat | tgtctcagct | gtagccagtg | tattgaacac | gtttatacgc | gacgggaccc | 420 |
| cactgagacc | aggagtggag | aagcgcctgc | agtcgccgta | tctccgacgt | ttggcttatc | 480 |
| ccgaggcact | tcgactggca | atggactatc | acatgtaacc | tggcgttcgg | atgacgcact | 540 |
| gttgcggctt | ttccgcagtc | acggtgcaat | cgggaactcc | agaggggggat | gccagcagga | 600 |
| aactcgagtg | tgggtgggtt | ctgtagcagc | ggatggttgt | cctttctact | gaccaatagt | 660 |
| cgcaccgcac | gaacgctaca | agtggcgcca | ccagtggtgt | ttggtccgtg | ttaacggagg | 720 |
| aacgactttg | tttcagcaac | ccccgngcag | ccaaacgcac | tcgactagtc | gctggcgtga | 780 |
| acgtgtcaag | tcgatgaccc | taaaaaaaaa | aaaaaaaaaa | aa | | 822 |

<210> SEQ ID NO 14
<211> LENGTH: 122
<212> TYPE: PRT
<213> ORGANISM: Sarcocystis neurona

<400> SEQUENCE: 14

Met Pro Arg Leu Pro Leu Leu Lys His Leu Leu Val Ala Thr Phe Leu
1               5                   10                  15

Leu Ala Gly Gly Ser Gly Val Leu Cys Gly Glu Arg Gly Glu Leu Gly
                20                  25                  30

Ala Ser Asn His Arg Gly Gly Gly Ser Val Asp Ile Pro Gly Ala Pro
            35                  40                  45

Gln Glu Ser Ala Val Val Glu Asp Gly Thr Glu Ala Asp Ser Asp Leu
        50                  55                  60

Arg Phe Glu Glu Arg Leu Ala Leu His Ile Val Ser Ala Val Ala Ser
65                  70                  75                  80

Val Leu Asn Thr Phe Ile Arg Asp Gly Thr Pro Leu Arg Pro Gly Val
                85                  90                  95

Glu Lys Arg Leu Gln Ser Pro Tyr Leu Arg Arg Leu Ala Tyr Pro Glu
            100                 105                 110

Ala Leu Arg Leu Ala Met Asp Tyr His Met
        115                 120

<210> SEQ ID NO 15
<211> LENGTH: 771
<212> TYPE: DNA
<213> ORGANISM: Sarcocystis neurona

<400> SEQUENCE: 15
gttactttgc acgtccttca cattcatgtt tcatttgtcg ctcaactgtc gcagggtttt     60
cagctttcga agtgcttctt gtgtacaaaa atttgcacac tcctgttccc ctttaactgg    120
caaccttgta caccaaaaaa agaaccttat caacgatgcc gcgactgtcg cttcttaacc    180
tcctggtgat ggcgacggcc ctcctcgctg ctggctctac cgtcttgtgc gcggaggaag    240
atgtaacagg aggtgacaat acagcaaacc cgccgcgaaa tccagcgggg ccactggaga    300
atccactacg gggcccactg gcggaactcg gagcgcgacg gttgatgaac tcattaggga    360
gacatgtaag gaacggttcg ctcttcttcg cgagtcttat cattgttgca gcgatgctcg    420
tcgactttgt gccagttgcg aacgcgcgca tggacaacgg gacacttgaa ctttaatttc    480
ttgacaggag acggccaaaa gcagaaaaga gctgtcctca aggctgaat acatcacaac    540 ggacataaca acacaacgga cgcgtggaca ccgccgagtt cggaaacaaa gtaattagtc    600
cgataattca tgagggttga ggccttagta ccactttctg tatggatata catgcttgct    660
gcttcgctgc gcgcttactt atcgaaaatg ctgtgccacc ggtgccagtg ctacacaagt    720
gtgttgcttg cctgcgccca cgtacacacg taatcggaat tcctgtatcg t             771

<210> SEQ ID NO 16
<211> LENGTH: 106
<212> TYPE: PRT
<213> ORGANISM: Sarcocystis neurona

<400> SEQUENCE: 16

Met Pro Arg Leu Ser Leu Leu Asn Leu Leu Val Met Ala Thr Ala Leu
1               5                   10                  15

Leu Ala Ala Gly Ser Thr Val Leu Cys Ala Glu Glu Asp Val Thr Gly
            20                  25                  30

Gly Asp Asn Thr Ala Asn Pro Pro Arg Asn Pro Ala Gly Pro Leu Glu
        35                  40                  45

Asn Pro Leu Arg Gly Pro Leu Ala Glu Leu Gly Ala Arg Arg Leu Met
    50                  55                  60

Asn Ser Leu Gly Arg His Val Arg Asn Gly Ser Leu Phe Phe Ala Ser
65                  70                  75                  80

Leu Ile Ile Val Ala Ala Met Leu Val Asp Phe Val Pro Val Ala Asn
                85                  90                  95

Ala Arg Met Asp Asn Gly Thr Leu Glu Leu
            100                 105

<210> SEQ ID NO 17
<211> LENGTH: 755
<212> TYPE: DNA
<213> ORGANISM: Sarcocystis neurona

<400> SEQUENCE: 17
tgcctgcttc gcaaggccaa actgagttct acgtacacaa atctggtcct ttcgccttcc     60

-continued

| | |
|---|---|
| cctcggtcgg cagcgttgtt acgcaccaga acagtcacat cagcaatgcc gcgcttgccg | 120 |
| ctccttaagc acctcttggt ggccacgttc ctcctcgctg gtggctccgg cgtcctgtgc | 180 |
| ggggaaagag gagagctcgg agcaagtaac accgtggcg gcgggagtgt ggatatccct | 240 |
| ggagctcctc aggagtcggc agtcgtagag gatgggacag aagcaggtga gcggctgtct | 300 |
| cattactgtt aacgcagctg tagcgaatgt gttggacaag attatatgaa gcttttttgc | 360 |
| acttgcggtg aaactgggga cgccagcagg aaacttgagt gtgggagaat tctggagcag | 420 |
| cgaatggatc tgcttaattg acagcaatcg ttcacaacga cgtgacaact ggtgccttca | 480 |
| ggggcgtgtg gtcacagcgc aactatagga gctcggcagt cctcggaatc aatgcgtgaa | 540 |
| gctgattacc ctatacacct caaagacgtg gcctcaatcc ctctgctgat acgtatactt | 600 |
| ttctgcgtcc tttcgctgag ccgagactca cctgaatctt tggcactgtt gtacgtgtga | 660 |
| gttgcttggc tggtcccgta cccatggaat cggaacttct gtaacccagg tggtcgccac | 720 |
| gacgataatg tttagctggg cccacactca tctag | 755 |

<210> SEQ ID NO 18
<211> LENGTH: 68
<212> TYPE: PRT
<213> ORGANISM: Sarcocystis neurona

<400> SEQUENCE: 18

Met Pro Arg Leu Pro Leu Leu Lys His Leu Leu Val Ala Thr Phe Leu
1               5                   10                  15
Leu Ala Gly Gly Ser Gly Val Leu Cys Gly Glu Arg Gly Glu Leu Gly
            20                  25                  30
Ala Ser Asn His Arg Gly Gly Gly Ser Val Asp Ile Pro Gly Ala Pro
        35                  40                  45
Gln Glu Ser Ala Val Val Glu Asp Gly Thr Glu Ala Gly Glu Arg Leu
    50                  55                  60
Ser His Tyr Cys
65

<210> SEQ ID NO 19
<211> LENGTH: 811
<212> TYPE: DNA
<213> ORGANISM: Sarcocystis neurona

<400> SEQUENCE: 19

| | |
|---|---|
| tgcctgcttc gcaaggccaa actgagttct acgtacacaa atctggtcct ttcgccttcc | 60 |
| cctcggtcgg cagcgttgtt acgcaccaga acagtcacat cagcaatgcc gcgcttgccg | 120 |
| ctccttaagc acctcttggt ggccacgttc ctcctcgctg gtggctccgg cgtcctgtgc | 180 |
| ggggaaagag gagagctcgg agcaagtaac ctccgtggcg gcgggagtgt gtatacccct | 240 |
| gaagctcctc aggagtcggc agtcgtagag gcagggacag aagaagactc aggagttgcg | 300 |
| actctggagt tgcgagacgc gttgagtgag gtgggacagg ggatgcggat ggcattgcat | 360 |
| ggtatctcaa ctgtagttag cgtattggac ggtgttttag cgacatgtt cccagcgaca | 420 |
| gcagaacaga gggagcctat tcagttcccg catctccaac gtttgcttcg tcgactggca | 480 |
| atggactaac acgtgtaacc tggcgttcgg atgacgcact gttgcggctt ttccgctgtc | 540 |
| acggtgcaat cgggaactcc agagggggat gccagcagga aactcgagtg tgggtgggtt | 600 |
| ctgtagcagc ggatggttgt catttctatt gaccaacagt cgcaccgcac gaacgctaca | 660 |
| agtggcgcca ccagtggtgt ttggtccgtg tcagcggatg aacgactttg tttcagcaac | 720 |

```
cccccgcgcag ccaaacgcag tcgacagtcg ctggtgtgaa cgtgtcaagt cgattaaact      780
aaaaaaaaaa aaaaaaaaaa aaaaaaaaaa a                                      811
```

<210> SEQ ID NO 20
<211> LENGTH: 127
<212> TYPE: PRT
<213> ORGANISM: Sarcocystis neurona

<400> SEQUENCE: 20

```
Met Pro Arg Leu Pro Leu Leu Lys His Leu Leu Val Ala Thr Phe Leu
1               5                   10                  15

Leu Ala Gly Gly Ser Gly Val Leu Cys Gly Glu Arg Gly Glu Leu Gly
            20                  25                  30

Ala Ser Asn Leu Arg Gly Gly Ser Val Tyr Thr Pro Glu Ala Pro
        35                  40                  45

Gln Glu Ser Ala Val Val Glu Ala Gly Thr Glu Glu Asp Ser Gly Val
    50                  55                  60

Ala Thr Leu Glu Leu Arg Asp Ala Leu Ser Glu Val Gly Gln Gly Met
65                  70                  75                  80

Arg Met Ala Leu His Gly Ile Ser Thr Val Val Ser Val Leu Asp Gly
                85                  90                  95

Val Leu Gly Asp Met Phe Pro Ala Thr Ala Glu Gln Arg Glu Pro Ile
            100                 105                 110

Gln Phe Pro His Leu Gln Arg Leu Leu Arg Arg Leu Ala Met Asp
        115                 120                 125
```

<210> SEQ ID NO 21
<211> LENGTH: 1493
<212> TYPE: DNA
<213> ORGANISM: Sarcocystis neurona

<400> SEQUENCE: 21

```
ggggaggtaa gtgttggcgg taatgctgca tcattagggt cagacacgct gtccatctgt       60
cattctcgcc agaatgacga gggcggtgct gctgacgttt ctgacactct gctccgccag      120
agtgtccctt gtgagggccg gagcgccgcc tcaagcaacg tgcgccaatg gcgaaacgac      180
tgttactaag ctcggcagct ctggcgcact acgaatccac tgcccaaata attttcgact      240
cgcgccccgg gctgggaatg acgccggtca gatgcaggtc tatgcaactg cggttgctga      300
gaatcctgta acatacgag acgtcctgcc cggcgcatct tacctctctg tacagaacgt       360
cccgaccctc accgtcccgc aattgcccgc caaagctacg agcgtctttt ttcactgcca      420
gcagcaaccc gacaaccaat gcttcatcca ggtagaagta gcgccggctc cgcgcctagg      480
tccgaatacc tgcgcggcgc tgcagtccac gatcgccttc gaagttcaac aagcgaatga      540
aacagcagtc ttcagctgcg gcgagggact tgctgtgttc ccgcaaggta gcaaagcgtt      600
ggatgaagcc tgctccaaag agcaggccct acccagtggc gccgctttag ctccaaagga      660
tggtgggctc caccttggtt ttcctcagct tcctcagcag gctatgaaga tttgctatat      720
ttgtacgaat ggtggtgtgc aggcagaggc ggcccaacgg tgtgaggttc gcatctccgt      780
cgcagcgaac ccagacggaa gcgttccagg ggctaacgga gccgcctctc taggagctgc      840
cgcacgcagc gcctctgcgt tagggttggc tctcgttgca ggcgctttct tgcacttttg      900
ctaatcctgc cgtgtagcgt ctctggtggc ccgccccaca gatcctggtt attcccacag      960
ctgccaaaag gggcaacgac cgctccaaga gcatgcctag acgcgttcag taacgtgcct     1020
actgttccaa aacgggaaaa tccgaagatg caaaattcat ccggtgcagc gtcccatgtg     1080
```

-continued

```
ttcagttacg actggacgag tgtagtcaca tggttttaca tccattcgca gtgcagaggc    1140
gtgggctcgc atattttttt tgtagtgtgc cgttgtagat ccagcaagtt aaatatgtta    1200
ttcattttga gcgcctgttc cacgtaggcg gctggaaaat tttctgggcg ctcgtcggtg    1260
cgccatagca gcaaccagtt agtagcttgc agtgccatga cgcggtctca agatggttca    1320
acagttgcag ttatcagcct ccataggttt taatggcagc gttaccaacg ggctgctttt    1380
caatccagat cgcgtgtcag tttcatatgg aactgggtcc gcagtcgtta tacgaaattt    1440
ggtgtcgaac gatcaaattt tccttcacgg tcaaaaaaaa aaaaaaaaaa aaa           1493
```

<210> SEQ ID NO 22
<211> LENGTH: 276
<212> TYPE: PRT
<213> ORGANISM: Sarcocystis neurona

<400> SEQUENCE: 22

```
Met Thr Arg Ala Val Leu Leu Thr Phe Leu Thr Leu Cys Ser Ala Arg
1               5                   10                  15

Val Ser Leu Val Arg Ala Gly Ala Pro Pro Gln Ala Thr Cys Ala Asn
            20                  25                  30

Gly Glu Thr Thr Val Thr Lys Leu Gly Ser Ser Gly Ala Leu Arg Ile
        35                  40                  45

His Cys Pro Asn Asn Phe Arg Leu Ala Pro Arg Ala Gly Asn Asp Ala
    50                  55                  60

Gly Gln Met Gln Val Tyr Ala Thr Ala Val Ala Glu Asn Pro Val Asn
65                  70                  75                  80

Ile Arg Asp Val Leu Pro Gly Ala Ser Tyr Leu Ser Val Gln Asn Val
                85                  90                  95

Pro Thr Leu Thr Val Pro Gln Leu Pro Ala Lys Ala Thr Ser Val Phe
            100                 105                 110

Phe His Cys Gln Gln Gln Pro Asp Asn Gln Cys Phe Ile Gln Val Glu
        115                 120                 125

Val Ala Pro Ala Pro Arg Leu Gly Pro Asn Thr Cys Ala Ala Leu Gln
    130                 135                 140

Ser Thr Ile Ala Phe Glu Val Gln Gln Ala Asn Glu Thr Ala Val Phe
145                 150                 155                 160

Ser Cys Gly Glu Gly Leu Ala Val Phe Pro Gln Gly Ser Lys Ala Leu
                165                 170                 175

Asp Glu Ala Cys Ser Lys Glu Gln Ala Leu Pro Ser Gly Ala Ala Leu
            180                 185                 190

Ala Pro Lys Asp Gly Leu His Leu Gly Phe Pro Gln Leu Pro Gln
        195                 200                 205

Gln Ala Met Lys Ile Cys Tyr Ile Cys Thr Asn Gly Gly Val Gln Ala
    210                 215                 220

Glu Ala Ala Gln Arg Cys Glu Val Arg Ile Ser Val Ala Ala Asn Pro
225                 230                 235                 240

Asp Gly Ser Val Pro Gly Ala Asn Gly Ala Ser Leu Gly Ala Ala
                245                 250                 255

Ala Arg Ser Ala Ser Ala Leu Gly Leu Ala Leu Val Ala Gly Ala Phe
            260                 265                 270

Leu His Phe Cys
        275
```

<210> SEQ ID NO 23

-continued

<211> LENGTH: 975
<212> TYPE: DNA
<213> ORGANISM: Sarcocystis neurona

<400> SEQUENCE: 23

```
atgtaccctt gcggcgagcg gcgttttcag attgtaacgt gacatagtcc tgggtcctct     60
tcagggcagg cgtctcgcag ttgtggtgtc ggtgtacgtg ttcataattt tcacagcctg    120
cttgcagccg tgttggattt ttgctgccaa tatcccaccg tccacgctct caacatggag    180
actccccgat gcattcttgc ctgcgctgca ggcatagcag cagttattat ttgcagttct    240
ttctccgtcg cgtcggccca agtcgcaaca attgcgtgca cacaagctgg aatgacccct    300
gtttctctgg gccccggtca gagctttgtg ctgaactgcc aggcaccctt taccatagcg    360
acgcctgcca actttcacac ccacgcttgt gcgggcactg gtgccaattg tcagaatcct    420
gaaacgtacg ccaagttgtt cccaaaggcg tccaaccacg tgtgggtgag tccagcggac    480
agcactagtg cgactcatac ctggacggca cccgctgcga accagttgag cggcaaaact    540
gtgtttagtg tgggatgcac cagtacaggc gacccagccg ggatctgcgc cgtcgacgtg    600
acagtttcca gctcagtgaa gacagtcgct tctggtgtcc tgcttgcaat gtgttcactc    660
gcatctctca cagtgttgta aggtgtgaag atgaaattgt ccccgtgcgg cagagccttc    720
tgaaggtacg taatcggggc ctgggaaggc gtgcaggttt gagatacatc ggtgtacagc    780
acacttgcct tcgtttttca aacgcacgaa gtgtgacgta cggtttgaac tctgtgcatc    840
cgaccgtatt ttttgcgcac gtaaccggta cctgcgtccg cgaaacattt tttgctgatt    900
tggtgggaaa gacactattg ctgtttttcg aggccttggc tgatgtgcta aaagggtggg    960
caaaaaaaaa aaaaa                                                     975
```

<210> SEQ ID NO 24
<211> LENGTH: 168
<212> TYPE: PRT
<213> ORGANISM: Sarcocystis neurona

<400> SEQUENCE: 24

```
Met Glu Thr Pro Arg Cys Ile Leu Ala Cys Ala Ala Gly Ile Ala Ala
1               5                   10                  15

Val Ile Ile Cys Ser Ser Phe Ser Val Ala Ser Ala Gln Val Ala Thr
            20                  25                  30

Ile Ala Cys Thr Gln Ala Gly Met Thr Pro Val Ser Leu Gly Pro Gly
        35                  40                  45

Gln Ser Phe Val Leu Asn Cys Gln Ala Pro Phe Thr Ile Ala Thr Pro
    50                  55                  60

Ala Asn Phe His Thr His Ala Cys Ala Gly Thr Gly Ala Asn Cys Gln
65                  70                  75                  80

Asn Pro Glu Thr Tyr Ala Lys Leu Phe Pro Lys Ala Ser Asn His Val
                85                  90                  95

Trp Val Ser Pro Ala Asp Ser Thr Ser Ala Thr His Thr Trp Thr Ala
            100                 105                 110

Pro Ala Ala Asn Gln Leu Ser Gly Lys Thr Val Phe Ser Val Gly Cys
        115                 120                 125

Thr Ser Thr Gly Asp Pro Ala Gly Ile Cys Ala Val Asp Val Thr Val
    130                 135                 140

Ser Ser Ser Val Lys Thr Val Ala Ser Gly Val Leu Leu Ala Met Cys
145                 150                 155                 160
```

Ser Leu Ala Ser Leu Thr Val Leu
                165

<210> SEQ ID NO 25
<211> LENGTH: 1585
<212> TYPE: DNA
<213> ORGANISM: Sarcocystis neurona
<220> FEATURE:
<221> NAME/KEY: misc_feature
<222> LOCATION: (1064)..(1064)
<223> OTHER INFORMATION: n is a, c, g, or t
<220> FEATURE:
<221> NAME/KEY: misc_feature
<222> LOCATION: (1114)..(1114)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1502)..(1502)
<223> OTHER INFORMATION: n is a, c, g, or t
<220> FEATURE:
<221> NAME/KEY: misc_feature
<222> LOCATION: (1508)..(1508)
<223> OTHER INFORMATION: n is a, c, g, or t
<220> FEATURE:
<221> NAME/KEY: misc_feature
<222> LOCATION: (1510)..(1510)
<223> OTHER INFORMATION: n is a, c, g, or t
<220> FEATURE:
<221> NAME/KEY: misc_feature
<222> LOCATION: (1512)..(1513)
<223> OTHER INFORMATION: n is a, c, g, or t
<220> FEATURE:
<221> NAME/KEY: misc_feature
<222> LOCATION: (1517)..(1517)
<223> OTHER INFORMATION: n is a, c, g, or t
<220> FEATURE:
<221> NAME/KEY: misc_feature
<222> LOCATION: (1520)..(1520)
<223> OTHER INFORMATION: n is a, c, g, or t
<220> FEATURE:
<221> NAME/KEY: misc_feature
<222> LOCATION: (1525)..(1528)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1539)..(1539)
<223> OTHER INFORMATION: n is a, c, g, or t
<220> FEATURE:
<221> NAME/KEY: misc_feature
<222> LOCATION: (1543)..(1545)
<223> OTHER INFORMATION: n is a, c, g, or t
<220> FEATURE:
<221> NAME/KEY: misc_feature
<222> LOCATION: (1550)..(1550)
<223> OTHER INFORMATION: n is a, c, g, or t
<220> FEATURE:
<221> NAME/KEY: misc_feature
<222> LOCATION: (1554)..(1554)
<223> OTHER INFORMATION: n is a, c, g, or t
<220> FEATURE:
<221> NAME/KEY: misc_feature
<222> LOCATION: (1557)..(1558)
<223> OTHER INFORMATION: n is a, c, g, or t

<400> SEQUENCE: 25

| | | | | |
|---|---|---|---|---|
| catttccccc | atcacctgcc | gtcaaggacg | tttttccctg | taaagaccat ttcaatcacc | 60 |
| gtgcgtctcc | ccctgccttt | ctggtctctt | acatctgcga | agatgatgaa aacttcgttt | 120 |
| ctgtcgctcg | cagttgcctg | ccttgtgtgg | gccctgtac | attgcattgc cgcagatcca | 180 |
| cctgttgcaa | cttgtgtgtc | cagggatgac | agtccgacac | aaacatatca actggcatca | 240 |
| attgggcaag | tgagaattac | atgcccagga | ggaactactt | tagcaaatag ggggcggag | 300 |
| caagccgata | acgcccgac | ggcagaggtt | tactctgaag | cggacgctgg aaaaacgtc | 360 |
| gcgttgaata | ctttgttggt | tggtgggacc | tacgttcggg | cggacgccaa tgacaacctc | 420 |
| acagtctcgc | agctgcccac | caaagcagtg | acggtgcttt | tcctctgtaa caggcagcct | 480 |
| ggccctggtg | ttggatgctg | gattgctgtt | gaagtcgcgg | ctcagcctcc tctgggacca | 540 |
| caggcttgta | cggttggtgg | aagcgaggta | acgttgactg | taacagctgc aaacgccacc | 600 |
| gcccagttcg | cctgtgccgc | tacgaagaac | gtatttccag | aaggcacaaa tgttacaac | 660 |
| tcggattgta | aaacggaaac | ccctttaagc | actgcattgc | caggtccac gctcacccgt | 720 |
| ggaaacatga | atgcgctaaa | aattcctacg | ttgccttcgg | ctgcaaagaa cctttgcttc | 780 |
| gtgtgtgcaa | caaatgttgg | ggacgaagcc | aaccaaaagt | gcagcgttaa aattaatgtg | 840 |
| agtggcagcc | ctcagggtgg | tgggaacggg | tccgtgggat | tgacagcacg ggctgcctcg | 900 |
| gcattaggga | ttctcatggt | cggagcagcg | ttggttcgaa | atgtttaagg cggaattacg | 960 |
| ctcgccagac | ttcacaaact | agtccttcta | tcgcatgact | gagcatgttc ttcatggctg | 1020 |
| cttctgtacc | gaagtcaccc | acgtggtgcg | ttaatcagaa | tacntgcaga tggtctttgg | 1080 |
| ggagaattca | cgattcgtg | gatttcacgt | gaanacgtgt | caacagacgt gcatctggta | 1140 |
| ctgatttgtg | cattgtcgtc | gaanagacgt | gtggttggaa | acccgggtgc ctttcttgtt | 1200 |
| tcgaatccat | tcaaggtggt | attgtccgta | cacaactgta | tgtgagtgaa gtggcgaggg | 1260 |
| ggaatctgcc | aattttgtac | actgttgttg | tgcgtgtacg | ttacgacggc tcggcgatg | 1320 |
| cgtgccacac | ccatgtggat | tttgattaca | ggaaggtgcg | cacaaagcag catttttat | 1380 |
| gcggaaacaa | tttcgcggat | tagactcgcc | gccattcatt | gcagcatgca gaggcaccgt | 1440 |
| gtgggggggg | ccttcaagaa | acgcttttca | agctctcttt | tctcctcaaa aaaaccnata | 1500 |
| cnctaatnan | tnnaaaanatn | tcacnnnncn | tcntatatnc | aannnaaaan ctcntgnngg | 1560 |
| ggggcccgt | cccaaattcc | cctat | | | 1585 |

<210> SEQ ID NO 26
<211> LENGTH: 281
<212> TYPE: PRT
<213> ORGANISM: Sarcocystis neurona

<400> SEQUENCE: 26

```
Met Met Lys Thr Ser Phe Leu Ser Leu Ala Val Ala Cys Leu Val Trp
  1               5                  10                  15

Ala Pro Val His Cys Ile Ala Ala Asp Pro Pro Val Ala Thr Cys Val
             20                  25                  30

Ser Arg Asp Asp Ser Pro Thr Gln Thr Tyr Gln Leu Ala Ser Ile Gly
         35                  40                  45

Gln Val Arg Ile Thr Cys Pro Gly Gly Thr Thr Leu Ala Asn Arg Gly
     50                  55                  60
```

-continued

| | | | | | | | | | | | | | | | |
|---|---|---|---|---|---|---|---|---|---|---|---|---|---|---|---|
|Ala|Glu|Gln|Ala|Asp|Asn|Gly|Pro|Thr|Ala|Glu|Val|Tyr|Ser|Glu|Ala|
|65| | | | 70| | | | 75| | | | | | 80| |

Asp Ala Gly Lys Asn Val Ala Leu Asn Thr Leu Leu Val Gly Gly Thr
                85                  90                  95

Tyr Val Arg Ala Asp Ala Asn Asp Asn Leu Thr Val Ser Gln Leu Pro
            100                 105                 110

Thr Lys Ala Val Thr Val Leu Phe Leu Cys Asn Arg Gln Pro Gly Pro
            115                 120                 125

Gly Val Gly Cys Trp Ile Ala Val Glu Val Ala Ala Gln Pro Pro Leu
        130                 135                 140

Gly Pro Gln Ala Cys Thr Val Gly Gly Ser Glu Val Thr Leu Thr Val
145                 150                 155                 160

Thr Ala Ala Asn Ala Thr Ala Gln Phe Ala Cys Ala Ala Thr Lys Asn
                165                 170                 175

Val Phe Pro Glu Gly Thr Asn Val Tyr Asn Ser Asp Cys Lys Thr Glu
            180                 185                 190

Thr Pro Leu Ser Thr Ala Leu Pro Gly Ala Thr Leu Thr Arg Gly Asn
            195                 200                 205

Met Asn Ala Leu Lys Ile Pro Thr Leu Pro Ser Ala Ala Lys Asn Leu
210                 215                 220

Cys Phe Val Cys Ala Thr Asn Val Gly Asp Glu Ala Asn Gln Lys Cys
225                 230                 235                 240

Ser Val Lys Ile Asn Val Ser Gly Ser Pro Gln Gly Gly Asn Gly
                245                 250                 255

Ser Val Gly Leu Thr Ala Arg Ala Ala Ser Ala Leu Gly Ile Leu Met
            260                 265                 270

Val Gly Ala Ala Leu Val Arg Asn Val
            275                 280

<210> SEQ ID NO 27
<211> LENGTH: 1111
<212> TYPE: DNA
<213> ORGANISM: Sarcocystis neurona
<220> FEATURE:
<221> NAME/KEY: misc_feature
<222> LOCATION: (267)..(267)
<223> OTHER INFORMATION: n is a, c, g, or t

<400> SEQUENCE: 27

```
gaggtgaagt attaatgcca cgtactgctg tttcgtatgc tacctgtcaa taccatacct    60
cggcgtcacc ctattgggaa cagtttccat cgaaaatgtt acgtgcgaca gtgttacgcg   120
cgacacttgt tgctactgcg gttatatacc ttgccggtcg tttacaatac gtcgtagcac   180
ggaaccccga gcaggctaca tgcgttctcg ggcaagcaac agcggtaaca gagcttgtaa   240
cattcggtgg cctcaatatt gtatgcncta acggttccac tttgcaacag gttcctgcgg   300 ccccagggggc ggccgacggg gcccagggcg cgggatatgt ttttcctca gatcaggaga   360 accgacaggg agtagttctc gaacaagtgg tgcctgggc tatcttcgca gtagggcaaa   420
ataatcagcc caacgttttg aacgtcgcgc agctgcccct ggcgcccag agcatttact   480 ttctgtgtcg tccacaagag aacgaacaac agacttgctt tatacgcgtg aatattcccg   540
cctcgcctcc tttgggaccg aatgcgtgtg tcgtacacaa taccgaggta cagttcaagg   600
cgggatccag caacgccacc gtccagttct cctgcggcaa cgccgcagca ctgcaaccac   660
aacaggctac taaaattttc gaccaaactt gtcagcaaga actggagcta gacacagtga   720
cccctggtgc gacgtgccag cggcctgcgg caggggggat ggttacagtg acgttcccgc   780
```

-continued

```
gcctgccgcc acaaaatcgg aaactctgct ttgtctgcac ccgcggacaa gagaattgca      840
aggttattat cgatgtagca gcggacccgg ccggtggtgc agctgtgggg atcacagctc      900
gtaccgcgtc ggcattgggt atcgtcgtcg ctgcagcagg cctcgtcggt gtgttctaac      960
ttcccgttcg cagagtcaac ggttgagtgg ttcttgtgga gacagccatt tgaataggtg     1020
gtggacggct gaaaggaaca gcttcgtcgc atggggagct gattatcgtt tcagcctaaa     1080
ctattggtgg accaaaaaaa aaaaaaaaaa a                                    1111
```

<210> SEQ ID NO 28
<211> LENGTH: 287
<212> TYPE: PRT
<213> ORGANISM: Sarcocystis neurona
<220> FEATURE:
<221> NAME/KEY: misc_feature
<222> LOCATION: (58)..(58)
<223> OTHER INFORMATION: Xaa can be any naturally occurring amino acid

<400> SEQUENCE: 28

```
Met Leu Arg Ala Thr Val Leu Arg Ala Thr Leu Val Ala Thr Ala Val
1               5                  10                  15

Ile Tyr Leu Ala Gly Arg Leu Gln Tyr Val Val Ala Arg Asn Pro Glu
            20                  25                  30

Gln Ala Thr Cys Val Leu Gly Gln Ala Thr Ala Val Thr Glu Leu Val
        35                  40                  45

Thr Phe Gly Gly Leu Asn Ile Val Cys Xaa Asn Gly Ser Thr Leu Gln
    50                  55                  60

Gln Val Pro Ala Ala Pro Gly Ala Ala Asp Gly Ala Gln Gly Ala Gly
65                  70                  75                  80

Tyr Val Phe Ser Ser Asp Gln Glu Asn Arg Gln Gly Val Val Leu Glu
                85                  90                  95

Gln Val Val Pro Gly Ala Ile Phe Ala Val Gly Gln Asn Asn Gln Pro
            100                 105                 110

Asn Val Leu Asn Val Ala Gln Leu Pro Ser Ala Pro Gln Ser Ile Tyr
        115                 120                 125

Phe Leu Cys Arg Pro Gln Glu Asn Glu Gln Gln Thr Cys Phe Ile Arg
    130                 135                 140

Val Asn Ile Pro Ala Ser Pro Leu Gly Pro Asn Ala Cys Val Val
145                 150                 155                 160

His Asn Thr Glu Val Gln Phe Lys Ala Gly Ser Ser Asn Ala Thr Val
                165                 170                 175

Gln Phe Ser Cys Gly Asn Ala Ala Ala Leu Gln Pro Gln Ala Thr
            180                 185                 190

Lys Ile Phe Asp Gln Thr Cys Gln Gln Glu Leu Glu Leu Asp Thr Val
        195                 200                 205

Thr Pro Gly Ala Thr Cys Gln Arg Pro Ala Ala Gly Gly Met Val Thr
    210                 215                 220

Val Thr Phe Pro Arg Leu Pro Pro Gln Asn Arg Lys Leu Cys Phe Val
225                 230                 235                 240

Cys Thr Arg Gly Gln Glu Asn Cys Lys Val Ile Ile Asp Val Ala Ala
                245                 250                 255

Asp Pro Ala Gly Gly Ala Ala Val Gly Ile Thr Ala Arg Thr Ala Ser
            260                 265                 270

Ala Leu Gly Ile Val Val Ala Ala Gly Leu Val Gly Val Phe
        275                 280                 285
```

-continued

<210> SEQ ID NO 29
<211> LENGTH: 1342
<212> TYPE: DNA
<213> ORGANISM: Sarcocystis neurona

<400> SEQUENCE: 29

```
cgtctcactg cctacttcta gaattatggg ataaggctca cccgatctcc ttctcataga      60
aagtaacttg cgtgttgcgg ctgcggtgga atcctggtat ctgcggtgaa attaccaacg     120
ctcctcgttg tcagcctgga gctgcgcacc aacgactttt tgcgctgcaa cagtgaacgc     180
gccagcagtc ctcgcgtttc cgggaagggc tcggcaattc tgcgtccgtt tttcagggtc     240
agcgggaacc atcatggcga actttgctct tcgctttgtc gcttttgtaa tcgtgtccgt     300
gttccacttg tgctcaagac ctgttcatgc gtcttttgaa accttcctaa cggcgcccat     360
aatacagtac ggcctctcag gatatccgct tgcggtgagg cactacattg cgtggctgga     420
tgtaatacaa caatgccaac ctccaactgt agatcgtgca ttgcagaccc aagaaggtca     480
ggaggcgtac actaaggctg ttgttgccgt gctactgggc gcactggatg aaggcgttaa     540
tgtacagcat aaggaatttt acatgcagct cctgaagaac atacagagcg cgccttctt      600
gaaggcgtta agagatgaga gtcagagagc catccttcag gagtacctag acaagaaggg     660
aagaagccgg ctcccccaag gattctcaaa taaggctgtt caaaccgcat cacacgtggg     720
ggttcttctg gtgacttgtg tcgcgttgcc gttggtatta atgcattaaa atccacttat     780
cccaccttc gttacgtgc gaacatcaaa cggaagtcgt tgacggtgga gggcgtttct     840
ttccggggc ttgagtccgc tcgtatccgt gcgttcctcg ccggttcaca catttgtgta     900
gagacctttt cgcctgaagt tctgaatgtc gttatggcct attccgttca gacgcgaact     960
tgcgacgagt gtctgttcga tcaagcgcgg tccgcactgt gtgacgcagc gaatccgcac    1020
agaggaagat gggggacgta atgggtgaac ccggaaaact cttacgggag agcgcatttt    1080
cgttgatgcc atttctaagt gtgtaacctc cttttggtgc gttgccacac attcgtaact    1140
gagggtactc ttacgtgcat ttcacccctg tctcggaaag gttggggttg taacttgtgg    1200
acacggaaat cttttacgg agaaagtatc tcttttcatg tcacttccgc ctctgtaacc    1260
ctcttttggg gggtggccaa acacgcgcaa ctgaggttat tgttacgtcc aaaaaaaaa     1320
aaaaaaaaa aaaaaaaaa aa                                               1342
```

<210> SEQ ID NO 30
<211> LENGTH: 171
<212> TYPE: PRT
<213> ORGANISM: Sarcocystis neurona

<400> SEQUENCE: 30

Met Ala Asn Phe Ala Leu Arg Phe Val Ala Phe Val Ile Val Ser Val
1               5                   10                  15

Phe His Leu Cys Ser Arg Pro Val His Ala Ser Phe Glu Thr Phe Leu
                20                  25                  30

Thr Ala Pro Ile Ile Gln Tyr Gly Leu Ser Gly Tyr Pro Leu Ala Val
            35                  40                  45

Arg His Tyr Ile Ala Trp Leu Asp Val Ile Gln Gln Cys Gln Pro Pro
        50                  55                  60

Thr Val Asp Arg Ala Leu Gln Thr Gln Glu Gly Gln Glu Ala Tyr Thr
65                  70                  75                  80

Lys Ala Val Val Ala Val Leu Leu Gly Ala Leu Asp Glu Gly Val Asn
                85                  90                  95

-continued

```
Val Gln His Lys Glu Phe Tyr Met Gln Leu Leu Lys Asn Ile Gln Ser
             100                 105                 110

Gly Ala Phe Leu Lys Ala Leu Arg Asp Glu Ser Gln Arg Ala Ile Leu
             115                 120                 125

Gln Glu Tyr Leu Asp Lys Lys Gly Arg Ser Arg Leu Pro Gln Gly Phe
         130                 135                 140

Ser Asn Lys Ala Val Gln Thr Ala Ser His Val Gly Val Leu Leu Val
145                 150                 155                 160

Thr Cys Val Ala Leu Pro Leu Val Leu Met His
                 165                 170
```

NUCLEIC ACIDS ENCODING *SARCOCYSTIS NEURONA* ANTIGEN AND USES THEREOF

The present application claims the benefit of priority of U.S. provisional patent application No. 60/357,479 filed Feb. 15, 2002.

FIELD OF THE INVENTION

The present Invention relates to nucleic acids of *Sarcocystis neurona*. In particular, the present invention relates to nucleic acids of *Sarcocystis neurona* and to nucleic acid reagents and antibodies for use in methods of detection and prevention of *Sarcocystis neurona* infection. More particularly, the present invention relates to novel nucleic acid sequences of *Sarcocystis neurona* and to utilization thereof including primers, probes, antigen/antibody diagnostic kits, vectors for production of peptides encoding the novel nucleic acids, and to antigenic proteins and vaccines against *Sarcocystis neurona*.

BACKGROUND OF THE INVENTION

*Sarcocystis neurona* is an apicomplexan parasite that is the primary cause of equine protozoal myeloencephalitis (EPM). Due to several factors, definitive pre-mortem diagnosis of EPM remains exceedingly difficult. In particular, the seroprevalence of *S. neurona* in horses is significant, yet the true incidence of EPM is quite low, thus indicating that infection does not equate with disease. Additionally, the immunoblot remains the only commercial assay available for testing samples from suspect EPM horses; while development of this test was a significant advance, it is a decade-old, first-generation assay that needs to be supplanted.

EPM is a common and debilitating infectious disease that affects the central nervous system of horses. The first detailed description of the disease was published in 1970 (Rooney et al., 1970), but it was not until 1991 that the etiological agent of EPM was isolated and designated *S. neurona* (Dubey et al., 1991). *S. neurona* is related to the human and animal pathogen *Toxoplasma gondii* and to the important veterinary pathogen *Neospora* spp. These species are phylogenetically classified into the Coccidia, which are all obligate intracellular parasites that produce a resistant oocyst during growth in the intestinal epithelium of their definitive host. Similar to other species of *Sarcocystis*, *S. neurona* has an obligatory heteroxenous life cycle, with the opossum (*Didelphis virginiana*) serving as a definitive host (Fenger et al., 1995). The intermediate host(s) include skunks (Cheadle et al., 2001b), raccoons (Dubey et al., 2001c), armadillos (Cheadle et al., 2001a), and cats (Dubey et al., 2000), although felids may be only an experimental intermediate host that does not contribute to the parasite life cycle in nature. Horses become infected with *S. neurona* by ingesting sporocysts in feces from the opossum, but unlike the normal intermediate hosts, mature sarcocysts have not been found in equine tissues (MacKay et al., 2000); consequently, the horse is currently considered an aberrant dead-end host. The geographic range of *S. neurona* appears to be limited to the Western Hemisphere, thus EPM primarily affects horses in the Americas.

Recent seroprevalence studies found that a significant proportion (45% to 55%) of horses have antibodies against *S. neurona* (Bentz et al., 1997; Blythe et al., 1997; Saville et al., 1997), suggesting that these animals are commonly exposed to the parasite. However, the incidence of EPM is estimated to be below 1% (MacKay et al., 2000), indicating that there is a clear dichotomy between simple infection with *S. neurona* and the occurrence of neurologic disease. In addition, early attempts at inducing disease by challenging horses with *S. neurona* sporocysts gave inconsistent results, and these studies were unable to authentically reproduce acute EPM (Cutler et al., 2001; Fenger et al., 1997). Consequently, it is apparent that other factors in addition to simple parasite infection are responsible for the progression to disease. It is well established that a robust cell-mediated immune response is important for controlling infections by coccidian parasites (Alexander et al., 1997; Baszler et al., 1999; Krahenbuhl and Remington, 1982), including *S. neurona* (Dubey et al., 2001a; Marsh et al., 1997), and it is possible that susceptibility to EPM may be increased in horses with inappropriate and/or suppressed immune responses during *S. neurona* infection. Accordingly, the use of stress to induce a transient immunosuppression has been shown to provide some improvement to the equine challenge model for EPM (Saville et al., 2001).

Definitive antemortem diagnosis of EPM remains exceedingly difficult, for a variety of reasons. Horses afflicted with EPM exhibit signs that are similar to a number of different neurological disorders (MacKay et al., 2000). Furthermore, *S. neurona* infection does not equate to disease, since only a small proportion of seropositive horses will suffer from EPM; as a consequence, the detection of anti-*S. neurona* antibodies in serum provides little diagnostic information other than previous exposure to the parasite. Analysis of cerebrospinal fluid (CSF) to reveal intrathecal antibody production, thus suggesting CNS infection, has improved the predictive value of antibody detection for EPM diagnosis. However, interpretation of CSF antibody presence can be confounded by contamination of the CSF sample with minute amounts of serum antibodies (Miller et al., 1999), and it is becoming apparent that the presence of antibodies in the CSF is not a definitive indication of active disease. Additionally, the contemporary diagnostic assays are hampered by several intrinsic problems, and they provide only mediocre predictive value for EPM diagnosis. Western blot analysis (a.k.a., immunoblot) of crude *S. neurona* lysate remains the immunodiagnostic test that is used to detect antibodies in suspect EPM horses (Granstrom et al., 1993). The continued use of the immunoblot has been necessitated by perceived antigenic cross-reactivity between different species of *Sarcocystis*, and the assay relies on the recognition of several antigens, primarily in the low molecular weight range, by serum/CSF antibodies (Dubey et al., 2001b; Granstrom et al., 1993; MacKay et al., 2000). Recent attempts to improve the immunoblot test have included the use of antibodies against the related parasite *Sarcocystis cruzi* to block cross-reactive epitopes, theoretically increasing the specificity of the immunoblot analysis for anti-*S. neurona* antibodies (Rossano et al., 2000). Unfortunately, western blot analysis is primarily a research tool that is relatively laborious and somewhat hindered by subjectivity, so any improvements to the immunoblot are of limited value. While the immunoblot has been utilized for a number of years to help diagnose EPM, it is a first-generation test that needs to be replaced with improved assays based on simplified, and thus more reliable, techniques that are more appropriate for diagnostic use. Nucleic acid amplification assays (polymerase chain reaction; PCR) for *S. neurona* detection have been developed based on the *S. neurona* ribosomal RNA genes (Fenger et al., 1994; Marsh et al., 1996). These PCR-based assays detect the presence of *S. neurona* DNA, and therefore the parasite, in the horse, so they can provide a definitive indication of active infection. However, prior to the present invention, these nucleic acid-based tests have been inherently unreliable. Specifically, parasites may be very few or non-existent in a CSF sample, so there will be no target molecules (i.e., parasite genomic DNA) for PCR amplification. More importantly, the general use of PCR for diagnosis is still suspect; although measures can be taken to improve the reliability of PCR, the technique continues to be troubled by both false positive and false negative results.

Research efforts directed toward understanding immunity against *S. neurona* infection and improving EPM diagnosis have been somewhat hampered by the lack of molecular information for *S. neurona*. The identification of *S. neurona*-specific antigens and characterization of the genes encoding these antigens as provided by the present invention hereby allow for the production of recombinant parasite antigens via expression in *E. coli* and the subsequent generation of monoclonal and monospecific polyclonal antibodies against the individual *S. neurona* antigens. The recombinant proteins and specific antibodies provided by the invention serve as valuable reagents for conducting immunological studies on *S. neurona* infections and the progression to EPM. Additionally, these reagents allow for the development of new and more reliable diagnostic tests; for example, a recombinant *S. neurona* antigen furnishes the key component for a simple and efficient enzyme-linked immunosorbent assay (ELISA) that can be used to monitor specific antibodies in equine serum or CSF. As provided by the teachings herein, the development of an ELISA that is based on a single recombinant *S. neurona* antigen rather than whole-parasite lysate provides a second-generation assay that significantly improves current methodologies for identifying *S. neurona*-infected animals. Notably, the use of a single antigen ELISA will allow for a more in-depth and complete dissection of antibody responses to *S. neurona*, which may distinguish between horses that have been simply exposed to the parasite versus horses that are actively infected and suffering from EPM.

A fluctuating equilibrium is maintained between the cell-mediated and the humoral (antibody) responses of the vertebrate immune system, and this balance will become biased, depending on the immune stimulus, in an effort to optimize the protective response. The two arms of the immune system are characterized by Th1 or Th2 lymphocytes that differ in their profile of secreted cytokines, and these immune factors target and regulate different effector cells and mechanisms. Immunoglobulin isotype switching is an important immune mechanism that allows the host to generate functional diversity in the humoral response, and the specific antibody isotype produced is largely controlled by the cytokines associated with the Th1 and Th2 balance (Finkelman et al., 1990). For example, in the mouse, a perturbation to the host that stimulates the immune system predominantly in the Th2 direction will generate an antibody response that is characterized by IgE and IgG1, whereas an immune response that is skewed towards a Th1 profile will be characterized by IgG2a and IgG3 (Finkelman et al., 1990; Snapper et al., 1997). It is generally believed that a Th1 cell-mediated response is necessary for control of coccidian parasites (Alexander et al., 1997; Krahenbuhl and Remington, 1982), so the role of antibody class switching for protection against *S. neurona* infection is unclear but may be secondary or unimportant. However, since the antibody isotypes produced during an infection will vary depending on the immune response that has been elicited, monitoring the relative levels of the specific isotypes will provide a means for assessing the nature of the immune response (i.e., Th1 versus Th2) in *S. neurona*-infected and EPM horses. The selection of an antigen for development of a diagnostic test can be somewhat subjective since any particular pathogen is composed of numerous antigenic proteins. Logically, the target molecule in a diagnostic assay must unfailingly elicit a detectable antibody response in the infected animal. A number of previous studies have demonstrated that surface antigens of the Coccidia are exceedingly immunogenic. In particular, the primary surface antigens of *Toxoplasma gondii* (Handman and Remington, 1980; Sharma et al., 1983) and *Neaspora caninum* (Howe et al., 1998) have been shown to be immunodominant. These surface antigens, designated SAGs and SAG-related sequences (SRSs), have been implicated in host cell attachment and invasion by the parasite (Dzierszinski et al., 2000; Grimwood and Smith, 1992; Hemphill, 1996; Mineo and Kasper, 1994; Mineo et al., 1993), most likely through interactions with sulfated proteoglycans on the host cell surface (He et al., 2002; Jacquet et al., 2001). In addition to their probable role as adhesins, there is increasing evidence that some of these surface antigens are involved in modulation of the host immune response (Lekutis et al., 2001). Significantly, the TgSAG1 surface antigen of *T. gondii* has been shown to protect mice against acute toxoplasmosis (Bulow and Boothroyd, 1991), and the NcSAG1 (p29) major surface antigen of *N. caninum* has been used to develop an ELISA for detection of Neospora infection in cattle (Howe et al., 2002). Collectively, these previous studies demonstrate that coccidian SAGs are at least candidate proteins for the development of both diagnostic assays and protective vaccines. Prior to the present invention, however, it had not been shown that the surface antigens of *S. neurona* (i.e., SnSAG2, SnSAG3, and SnSAG4) are effective target molecules for examining immune responses in infected horses and for developing improved assays for EPM diagnosis. The present invention utilizes recombinant *S. neurona* SAGs that are provided by the invention to provide simple and reliable ELISAs, and these assays can be used to scrutinize specific humoral immune responses in EPM horses and for detecting the presence of *S. neurona* in a test sample. Importantly, the developed ELISAs are valuable as tools to aid in the diagnosis of EPM infection in horses.

Nucleic acids of certain *Sarcocystis* and *Toxoplasma* species are known in the art. For example, Eschenbacher K-H et al. "Cloning and expression in *Escherichia coli* of cDNAs encoding a 31-kilodalton surface antigen of *Sarcocystis muris*". Molec. Biochem. Parasitol. 1992, 53:159–168 (1992). Eschenbacher discloses the cloning and expression of a surface coat protein of *Sarcocystis muris* merozoites consisting of 280 amino acids with a predicted size of 31 kDa.

Velge-Roussel F. et al. "Intranasal Immunization with *Toxoplasma gondii* SAG1 induces protective cells into both NALT and GALT compartments. Infection and Immunity, 2000, 68: 969–972, discloses that intra-nasal immunization with a SAG1 protein derived from *Toxoplasma gondii* plus a cholera toxin provides protective immunity in mice. Specific cellular response was achieved in nasal and mesenteric compartments after i.n. immunization. *T. gondii* naturally invading the intestine of its host, in this case the mouse, and can be partially controlled by i.n. immunization with the protein SAG1 plus CT.

Nielsen et al. discloses the construction of a DNA vaccine using the recombinant form of the surface coat protein SAG1 in *Toxoplasma gondii*, consisting of 824-nucleotides encoding the 275 amino acid protein. Animals immunized with this plasmid produce anti-SAG1 antibodies which recognize the native SAG1. See, Nielsen H. V et al. "Complete protection against lethal *Toxoplasma gondii* infection in mice immunized with a plasmid encoding the SAG1 gene". Infection and Immunity, 1999, 67: 6358–6363.

Peterson et al. discloses the use of an *E. coli* produced vaccine comprised of a recombinant *Toxoplasma gondii* SAG1 with alum as adjuvant, protecting mice against infection with *T. gondii*. Immunization with *E. coli* expressing rSAG1 in alum induced partial protective immunity against lethal infection with *T. gondii* in mice. See, Petersen E, Nielsen H V, Christiansen L, Spenter J. Immunization with *E. coli* produced recombinant *T. gondii* SAG1 with alum as adjuvant protect mice against lethal infection with *Toxoplasma gondii*. Vaccine. 1998 August;16(13):1283–9.

Bonenfant et al. discloses intranasal immunity with SAG1 and nontoxic mutant heat-labile enterotoxins protecting mice against *Toxoplasma gondii*. High level protection was assessed by the decreased load of cerebral cysts after challenge with the 76H strain of *T. gondii* from a group of mice immunized with LTR 72 plus SAG1 and LTK63 plus SAG1. See, Bonenfant C, Dimier-Poisson I, Velge-Roussel F, Buzoni-Gatel D, Del Giudice G, Rappuoli R, Bout D. "Intranasal immunization with SAG1 and nontoxic mutant heat-labile enterotoxins protects mice against *Toxoplasma gondii*". Infect Immun. 2001 March;69(3):1605–12.

Haumont et al. discloses that a recombinant form of *Toxoplasma gondii* SAG1 used in vaccination had a significant protective effect against maternofetal transmission of tachyzoites. Absence of parasites in fetuses was demonstrated in 66–86% of fetuses from adult guinea pigs. There was no quantitative correlation between anti-SAG1 antibody titers and protection against maternofetal transmission. This is reference also demonstrates that a subunit vaccine based on SAG1 confers a high degree of protection against congenital *T. gondii* infection. Haumont M, Delhaye L, Garcia L, Jurado M, Mazzu P, Daminet V, Verlant V, Bollen A, Beaumans R, Jacquet A. "Protective immunity against congenital toxoplasmosis with recombinant SAG1 protein in a guinea pig model". Infect Immun. 2000 September;68(9): 4948–53.

Angus et al. discloses that immunization with a DNA plasmid encoding the SAG1 (p30) protein of *Toxoplasma gondii* is immunogenic and protective in mice. Sera of immunized mice showed recognition of *T. gondii* tachyzoites by immunofluorescence and exhibited high titers of antibody to SAG1 by ELISA. This data suggest that nucleic acid vaccination can provide protection against *T. gondii* infection in mice. See, Angus C W, Klivington-Evans D, Dubey J P, Kovacs J A." Immunization with a DNA plasmid encoding the SAG1 (P30) protein of *Toxoplasma gondii* is immunogenic and protective in rodents". J Infect Dis. 2000 January;181(1):317–24.

Fort Dodge Animal Health, "Vaccine Development" discloses that an *S. neurona* merozoite culture that is chemically inactivated and incorporates an adjuvant is used as an EPM vaccine. This vaccine has been conditionally licensed for use but without any indication of its effectiveness in preventing *Sarcocyst neurona* induced EPM Fort Dodge Animal Health, "Vaccine Development" Discloses that an *S. neurona* merozoite culture that is chemically inactivated and incorporates an adjuvant is used as the EPM vaccine. Fort Dodge Animal Health, 20001.

Other references of interest include:Buxton D. "Protozoan infections in sheep and goats: recent advances" Vet. Res. 1998, 29 (3–4):289–310; O,Donoghue P J et al. "Attempted immunization of swine against acute sarcocystosis using cystozooite-derived vaccines". Vet. Immunol Immunopathol. 1985 January;8(1–2):83–92; Bulow R and Boothroyd J. C. "Protection of mice from fatal *Toxoplasma gondii* infection by immunization with p30 antigen in liposomes". J. Immunol. 1991, 147 3496–3500; Dame J B, MacKay R J, Yowell C A, Cutler T J, Marsh A, Greiner E C "*S. falcatula* from passerine and psittacine birds: synonymy with *S. neurona*, agent of EPM". J. Parasitol. 1995, December; 81(6):930–5; Mishima M, Xuan X, Shioda A, Omata Y, Fujisaki K, Nagasawa H, Mikami T. "Modified protection against *Toxoplasma gondii* lethal infection and brain cyst formation by vaccination with SAG2 and SRS1". J Vet Med Sci. 2001 April;63(4):433–8; Aosai F, Mun H S, Norose K, Chen M, Hata H, Kobayashi M, Kiuchi M, Stauss H J, Yano A. "Protective immunity induced by vaccination with SAG1 gene-transfected cells against *Toxoplasma gondii* infection in mice". Microbiol Immunol. 1999;43(1):87–91; Artois M, Cliquet F, Barrat J, Schumacher C L. "Effectiveness of SAG1 oral vaccine for the long-term protection of red foxes (Vulpes vulpes) against rabies". Vet Rec.1997, Jan. 18;140 (3):57–9; Follmann E H, Ritter D G, Baer G M. "Evaluation of the safety of two attenuated oral rabies vaccines, SAG1 and SAG2, in six Arctic mammals". Vaccine. 1996 March; 14(4):270–3; and Windeck T, Gross U." *Toxoplasma gondii* strain-specific transcript levels of SAG1 and their association with virulence". Parasitol Res. 1996;82(8):715–9.

Yet, despite the foregoing art, there remains a need in the art for a safe and effective vaccine against *Sarcocystis neurona*. Likewise, as set forth above there is also a need in the art for diagnostic kits including antigen and antibody kits for fast and reliable diagnosis of *Sarcocystis neurona* infection.

OBJECTS OF THE INVENTION

It is an object of the present invention to satisfy the need in the art by providing a novel isolated nucleic acid capable of encoding antigenic proteins derived from *Sarcocystis neurona*, or unique antigenic fragments thereof. It is also an object of the present invention to provide purified antigenic polypeptide fragments encoded by the novel nucleic acid sequences set forth herein that encode for *Sarcocystis neurona*. In particular, it is an object of the present invention to provide a purified antigenic polypeptide fragment encoded by the nucleic acid sequences set forth herein or a selective portion thereof, in a pharmaceutically acceptable carrier.

It is further an object of the present invention to provide isolated nucleic acids capable of selectively hybridizing with the nucleic acid from *Sarcocystis neurona* including, but not limited to, primers and probes for utilization in polymerase chain reaction (PCR) and other nucleic acid amplification techniques.

Another object of the invention is to provide a vector comprising the nucleic acid encoding *Sarcocystis neurona* or a unique fragment thereof and to provide the vector in a host capable of expressing the polypeptide encoded by that nucleic acid.

One important object of the invention is to provide a purified antibody that is selectively reactive with *Sarcocystis neurona* or an immunodominant polypeptide provided by the invention or a genetic variant thereof. A particular object of the present invention is to provide a purified monoclonal antibody specifically reactive with *Sarcocystis neurona* and a method of detection of *Sarcocystis neurona* utilizing the antibodies of the present invention.

SUMMARY OF THE INVENTION

The present invention satisfies the need in the art by providing a novel isolated nucleic acid encoding an antigenic protein derived from *Sarcocystis neurona*, or a unique fragment thereof. In one embodiment, the invention provides novel isolated nucleic acids encoding membrane-associated polypeptides SnSAG2, SnSAG3, and SnSAG 4.

The present invention also provides purified antigenic polypeptide fragments encoded by the novel nucleic acid sequences set forth herein that encode for *Sarcocystis neurona*. In one embodiment, the invention provides purified antigenic proteins or purified antigenic polypeptide fragments encoded by the novel nucleic acid sequences set forth herein that encode for SnSAG2, SnSAG3, and SnSAG 4. In another embodiment, the present invention provides a purified antigenic polypeptide fragment encoded by the nucleic acid sequences set forth herein or a selective portion thereof, in a pharmaceutically acceptable carrier.

The present invention also provides isolated nucleic acids capable of selectively hybridizing with the nucleic acid from *Sarcocystis neurona* including, but not limited to, primers and probes for utilization in polymerase chain reaction (PCR) and other nucleic acid amplification techniques.

Further, the present invention provides vectors comprising the isolated nucleic acids set forth herein encoding *Sarcocystis neurona* or a unique fragment thereof and provides the vector in a host capable of expressing the polypeptide encoded by that nucleic acid.

Finally, the present invention also provides a purified polyclonal and or a monoclonal antibody specifically reactive with *Sarcocystis neurona* and a method of detection of *Sarcocystis neurona* utilizing the antibodies of the present invention.

BRIEF DESCRIPTION OF THE DRAWINGS

FIG. 1 is a sequence comparison of mature SnSAG1 (SEQ ID NO.:31), SnSAG4 (SEQ ID NO.: 32), and SnSAG3 (SEQ ID NO.: 33) with SmMSA (SEQ ID NO.: 34) and TgSAG2E (SEQ ID NO.:35). The *S. neurona* surface antigens SnSAG1, SnSAG3 and SnSAG4 are most similar to the TgSAG2 family of *T. gondi* surface antigens. The sequences presented in the Figure are for the mature proteins after cleaving off the N-terminal signal peptide and the C-terminal signal for the GPI anchor. Sequence alignments of the predicted mature proteins revealed very moderate sequence identity (<25%). However, the SnSAGs contain 10/12 conserved cysteine residues that have been observed previously, suggesting that the SnSAGs have a tertiary structure that is similar to what has been determined for the TgSAGs/SRSs.

FIG. 2 is a sequence comparison of mature SnSAG2 (SEQ ID NO.: 36) with TgSAG1 (SEQ ID NO.: 37) and TgSRS2 (SEQ ID NO.: 38). The sequences presented in the Figure are for the mature proteins after cleaving off the N-terminal signal peptide and the C-terminal signal for the GPI anchor. The *S. neurona* surface antigen SnSAG2 is most similar to the TgSAG1 family of *T. gondii* surface antigens. Similar to the other SnSAGs, SnSAG2 shares modest sequence identity to its TgSAG orthologues, but contains 6/6 conserved cysteine residues that have been observed in each half of the prototypical two-domain apicomplexan SAG. SnSAG2 will also align with the carboxyl-terminal domain of the TgSAGs.

DETAILED DESCRIPTION OF THE INVENTION

Figure 3:
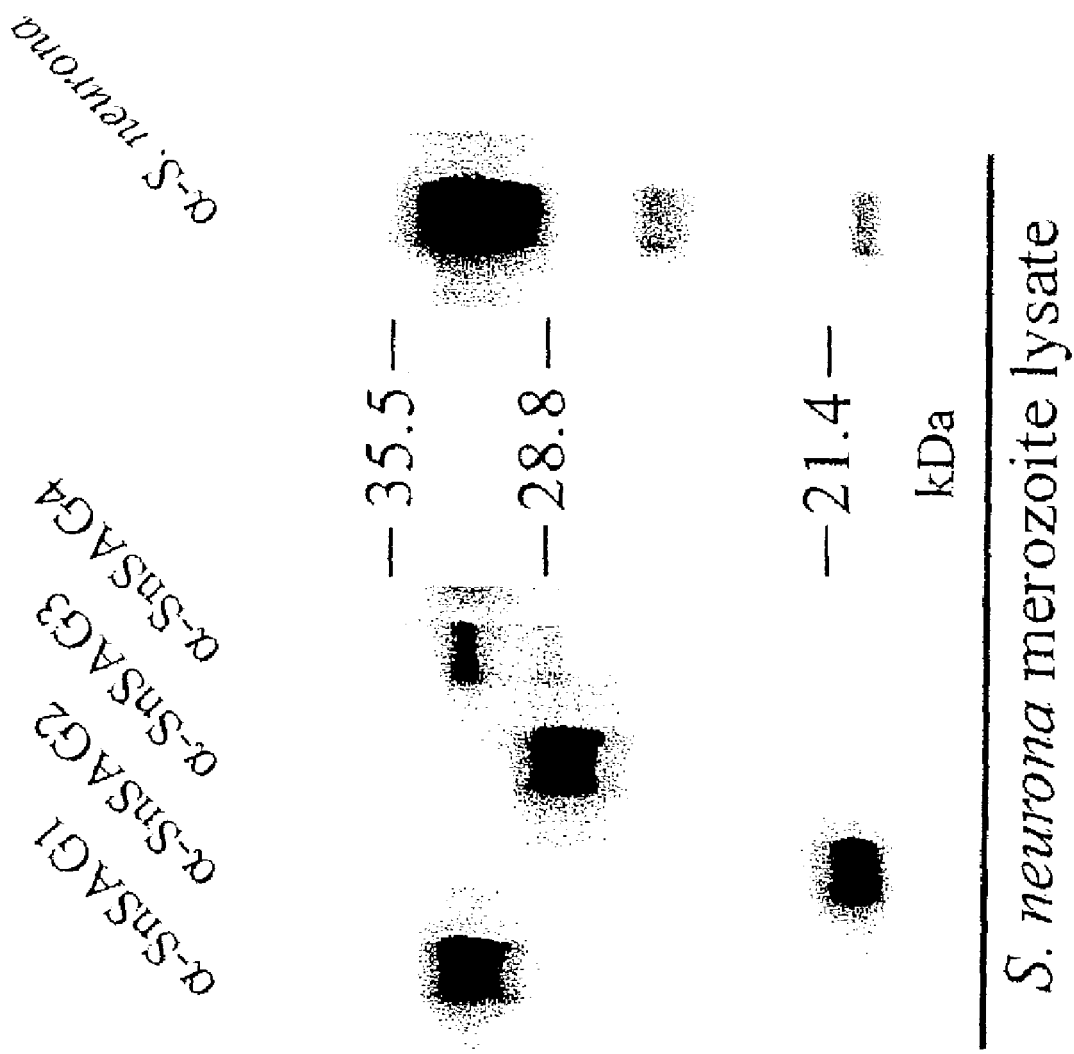
FIG. 3 shows a Western blot analysis of the Sn SAGs in *S. neurona* merozoites. The SnSAG genes were expressed in *E. coli*, and monospecific polyclonal antisera were generated against the recombinant proteins. Western blot analysis of reduced antigen revealed that each SnSAG migrated significantly higher than its predicted molecular weight, consistent with what has been observed for the *T. gondii* SAGs/SRS. SnSAG1 and SnSAG4 co-migrated and corresponded to the immunodominant band at about 30–32 kDa. SnSAG2 corresponded to an immunodominant band at approximately 18–20 kDa.

The present invention may be understood more readily by reference to the following detailed description of specific embodiments and the examples included therein. As used in the claims, "a" can mean one or more. As can be appreciated by one of skill in the art, methods and materials similar or equivalent to those described herein can be used in the practice of the present invention. All publications, patent applications, patents, and other references mentioned herein are incorporated by reference in their entirety. The disclosures of these publications in their entireties are hereby incorporated by reference into this application in order to more fully describe the state of the art to which this invention pertains. Although the present invention has been described with reference to specific details of certain embodiments thereof, it is not intended that such details should be regarded as limitations upon the scope of the invention except as and to the extent that they are included in the accompanying claims. In the case of a conflict with incorporated references, the present specification, including definitions will control. In addition, the particular embodiments discussed below are illustrative only and not intended to be limiting.

The present invention satisfies the long felt need in the art by providing novel isolated nucleic acid sequences which encode antigenic proteins derived from *Sarcocystis neurona*, or which encode unique antigenic protein fragments thereof. As used herein, a "nucleic acid" means a chain of at least two or more nucleotides such as DNA (deoxyribonucleic acid) or RNA (ribonucleic acid). As used herein, a "purified" nucleic acid is one that is substantially separated from other nucleic acid sequences in a cell or organism in which the nucleic acid naturally occurs. Likewise, by "isolated" nucleic acid is meant separated from at least some of other nucleic acids found in the naturally-occurring organism. The nucleic acids of the present invention can include positive and negative strand RNA as well as DNA. The above terms encompass double-stranded DNA, single-stranded DNA, and RNA and are meant to include genomic and subgenomic nucleic acids found in the naturally-occurring *Sarcocystis neurona* organism. The nucleic acids contemplated by the present invention include a nucleic acid having sequences from which a *Sarcocystis neurona* cDNA can be transcribed; or allelic variants and/or homologs of thereof. By "capable of selectively hybridizing" is meant a sequence which does not hybridize with other nucleic acids to prevent an adequate positive hybridization with nucleic acids from *Sarcocystis neurona* and is meant to include stringent hybridization conditions including low, moderate and high stringency conditions. Such stringency conditions are known in the artas, e.g., in U.S. Patent Publication No.: 2002/0115828 A1. By "unique fragment" is meant a fragment of the nucleic acids set forth in the Sequence Listing that is less than the full length that can selectively hybridize with a RNA, DNA or cDNA sequence derived from the novel sequences set forth herein or that can selectively hybridize with nucleic acids from *Sarcocystis neurona*. Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al. Methods Enzmol. 1987: 154–367, 1987). As one of skill in the art can appreciate, there can be naturally occurring allelic variants and non-naturally occurring variants or modifications of the nucleic acids of the invention. For example, homologs or naturally occurring allelic variants of the nucleic acids of the invention having from about 50% and up to about 99% sequence identity are contemplated by the invention. Likewise, it is contemplated that non-naturally occurring variants or modifications of the nucleic acids of the invention can range from about 50% to about 99% sequence identity to native *S. neurona* are contemplated.

In particular, one embodiment of the present invention provides isolated nucleic acid derived from three *Sarcocystis neurona* cluster sequences, namely Sn Cluster 144, Sn Cluster 21 and Sn Cluster 4, which comprise the nucleotide sequences set forth in the Sequence Listing as SEQ ID NOS: 1, 3, and 29 respectively and the sequences complimentary thereto. Also provided by the invention are the corresponding protein or polypeptide amino acid sequences for these three *Sarcocystis neurona* cluster sequences. The polypeptide sequence comprising Sn Cluster 144 is set forth in the Sequence Listing as SEQ ID NO: 2. The polypeptide sequence comprising Sn Cluster 21 is set forth in the Sequence Listing as SEQ ID NO: 4 and the polypeptide sequence comprising Sn Cluster 4 is set forth in the Sequence Listing as SEQ ID NO: 30. As used herein, the terms "polypeptide" and "protein" are used interchangeably and are meant to include any peptide-linked chain of amino acids, regardless of length or post-translational modification, e.g., glycosylation or phosphorylation. By "purified" polypeptide is meant a polypeptide that has been substantially separated or isolated away from other polypeptides in a cell, organism, or mixture in which the polypeptide occurs.

*Sarcocystis neurona* is an apicomplexan parasite that can cause a severe neurologic disease in horses called equine protozoal myeloencephalitis (EPM). Similar to other members of the Apicomplexa, *S. neurona* is an obligate intracellular pathogen that utilizes a number of unique structures and molecules (i.e., virulence factors) to support its parasitic life-style. Parasite surface molecules are virulence factors that are typically novel and undoubtedly important since they are responsible for the initial interactions with the host cell surface and host immune response. In *Toxoplasma gondii* for example, an extensive family of 25+ surface antigens has been identified, which are developmentally regulated and exhibit various levels of sequence similarity to either of the major *T. gondii* surface antigens TgSAG1 or TgSAG2. These surface molecules appear to be involved in receptor/ligand interactions with the host cell surface, and there is increasing evidence that some of the *T. gondii* SAGs are involved in modulation of host immune responses.

Figure 1:
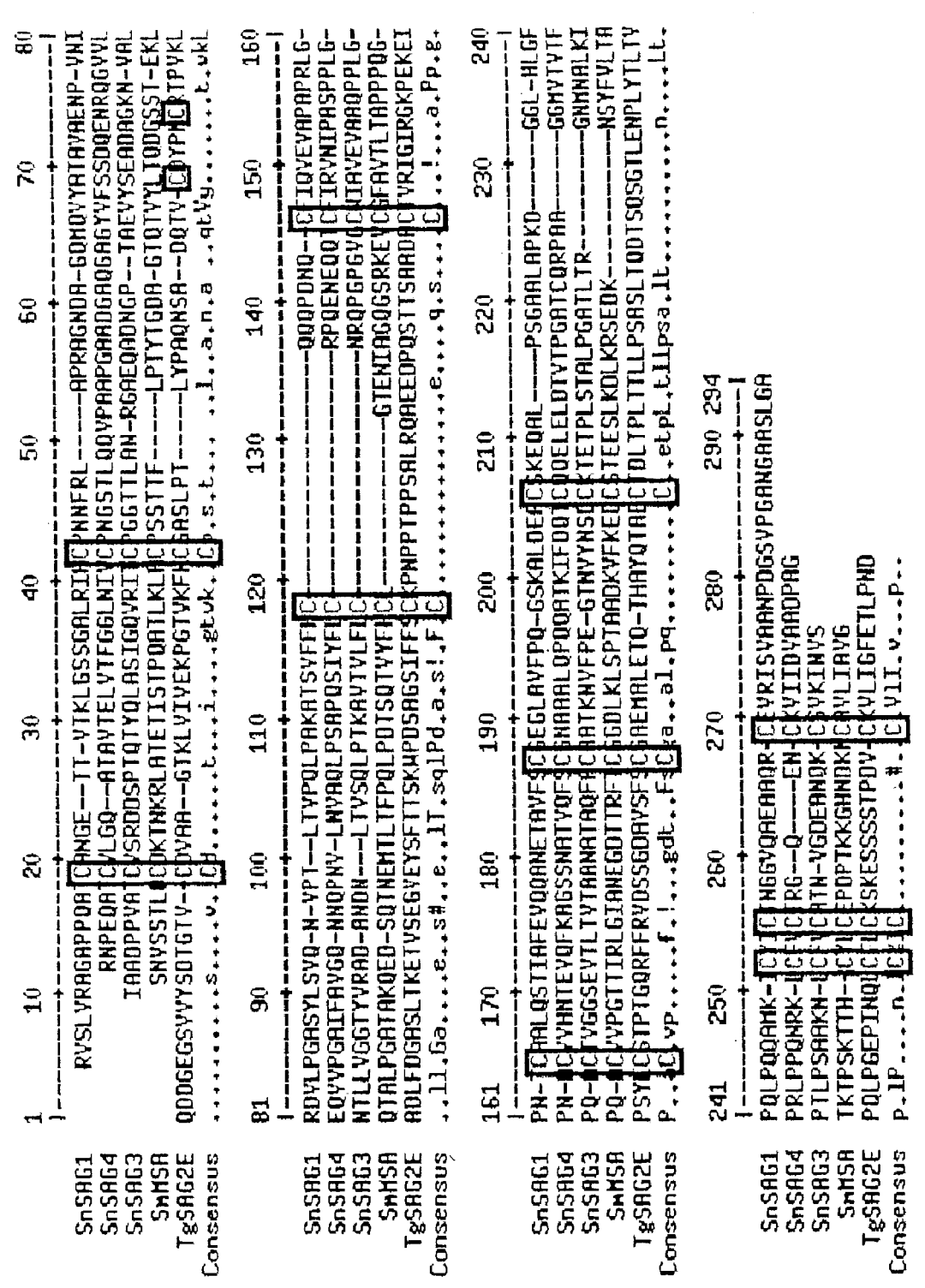
Figure 4:
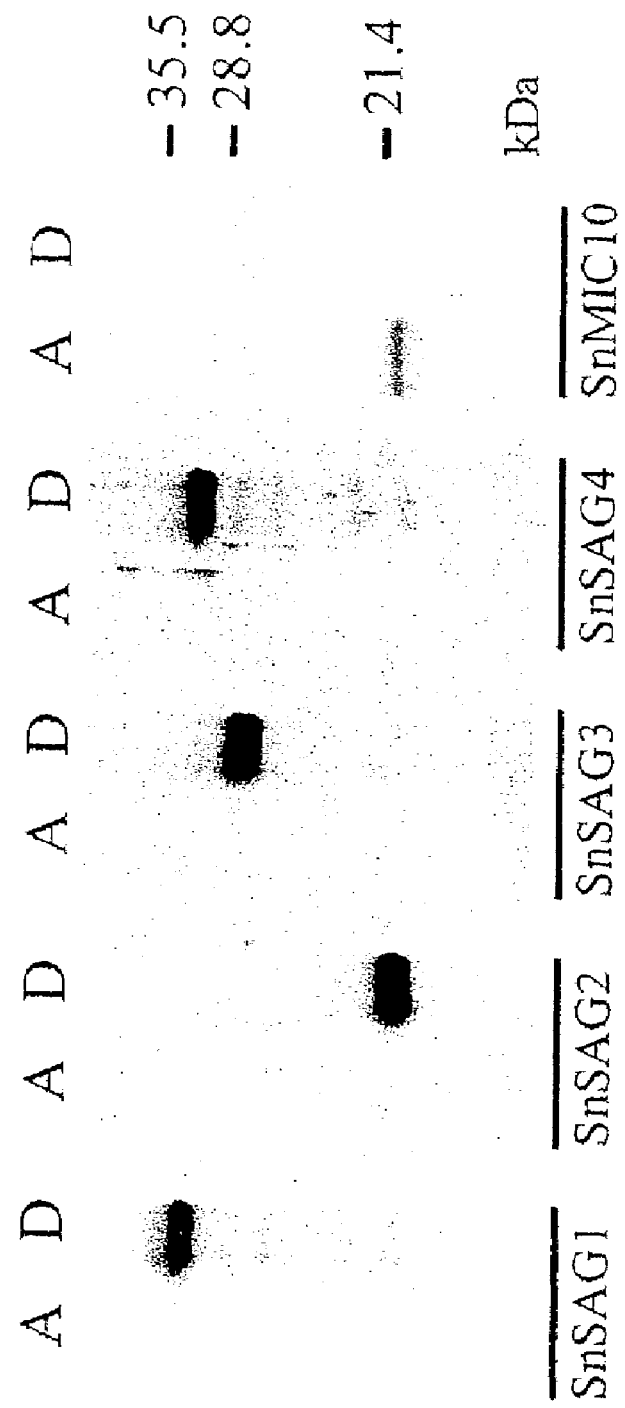
FIG. 4 shows the SnSAGs are membrane-associated in *Sarcocystis neurona* merozites. Triton X-114 partitioning assays indicated that the SnSAGs are associated with membranes, consistent with their surface localization via glycolipid anchoring. Western blot analysis of the partitioned proteins with the SnSAG-specific polyclonal antisera revealed that all four SnSAGs were separated exclusively into the detergent phase (D). The control protein, SnMIC10, was partitioned into the aqueous phase (A), as expected.
Figure 5:
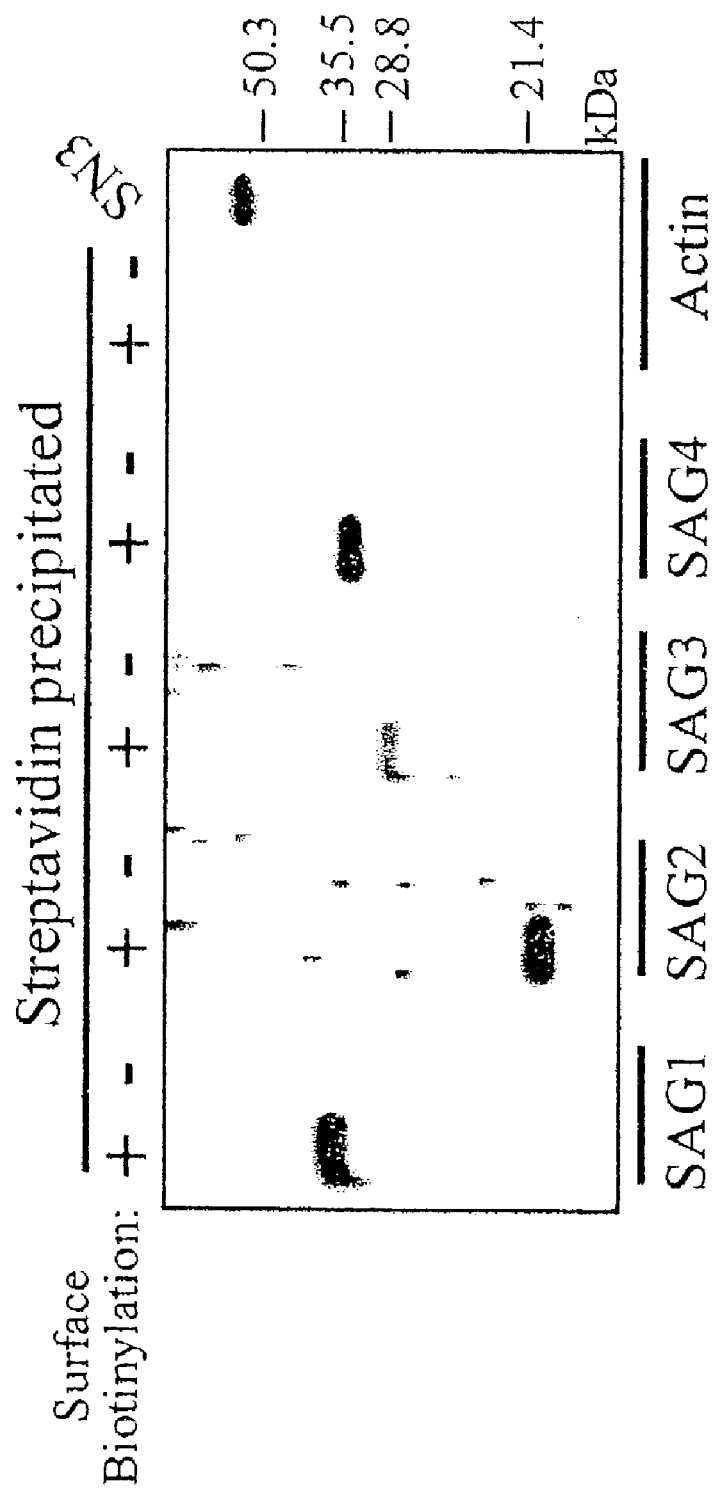
FIG. 5 shows that the four SnSAGs are displayed on the surface of *Sarcocystis neurona* merozoites. Surface biotinylation of *S. neurona* merozoites indicated that the four SnSAGs are displayed on the surface of the parasite. Western blot analysis with the SnSAG-specific antisera revealed each of the SnSAGs in the biotinylated protein fraction precipitated with immobilized streptavidin. The SnSAGs were not present in the non-labeled parasites, thus indicating that the streptavidin precipitation were specific for biotin-labeled proteins. The negative control protein (actin) was not detected in the biotin-labeled/streptavidin-precipitated protein fraction.

In one embodiment, the present invention provides identity and characterization of certain of the virulence factors of *S. neurona*. In particular, the present invention provides four isolated nucleic acids of *S. neurona* (genes) that encode parasitic surface antigens. A sequencing project was conducted that generated approximately 8500 expressed sequence tags (ESTs) from this organism. Examination of this sequence database has revealed a family of at least four *S. neurona* surface antigens that are orthologues of the SAG/SRS family of surface proteins in *T. gondii*. Based on their homology to the *T. gondii* SAGs, the novel *S. neurona* surface antigens have been designated SnSAG1, SnSAG2, SnSAG3, and SnSAG4 respectively. Each protein is predicted to contain an amino-terminal signal peptide and a carboxyl-terminal glycolipid anchor addition site, indicating surface localization, and Triton X-114 partitioning and surface biotinylation assays confirmed that all four proteins are membrane-associated and displayed on the *S. neurona* merozoite surface (See, FIGS. 4 and 5). Additionally, these novel *S. neurona* proteins possess multiple conserved cysteine residues that have been described previously for *T. gondii* SAGs and which are likely important for the tertiary structure of the proteins (See, FIGS. 1 and 2). Due to their surface localization and relative homology to *T. gondii* surface antigens, these *S. neurona* proteins have been designated SnSAG1, SnSAG2, SnSAG3, and SnSAG4.

Accordingly, one embodiment of the present invention comprises an isolated nucleic acid as set forth in the Sequence listing as SEQ ID NO: 21. The nucleic acid identified in SEQ ID NO: 21 comprises an 828-nucleotide open reading frame of the SnSAG1 gene of *Sarcocystis neurona* which encodes a 276 amino acid polypeptide set forth in the Sequence Listing as SEQ ID NO: 22. The polypeptide encoded by SEQ ID NO: 22 has a predicted amino-terminal signal peptide (indicating expression via the secretory pathway) and a glycolipid anchor addition site at the carboxy-terminal end (indicating surface localization). Database searches with the predicted protein sequence of SnSAG1 (rSnSAG1) revealed significant similarity (alignment score=80, E value=2×10–14) to a 31 kDa surface antigen from *Sarcocystis muris*.

A recombinant form of the *Sarcocystis neurona* SnSAG1 (rSnSAG1) has been expressed in *E. coli*. Western blot analysis of rSnSAG1 demonstrated that the recombinant antigen is recognized by antiserum from a rabbit that was immunized with *S. neurona* merozoites and by antibodies in cerebrospinal fluid (CSF) from an EPM (*Sarcocystis neurona* infected) horse (See, e.g., FIG. 3).

Another embodiment of the present invention comprises an isolated nucleic acid as set forth in the Sequence listing as SEQ ID NO: 23. The nucleic acid identified in SEQ ID NO: 23 comprises an 975 nucleotide open reading frame of the SnSAG2 gene of *Sarcocystis neurona* which encodes a 168 amino acid polypeptide set forth in the Sequence Listing as SEQ ID NO: 24.

The present invention also provides an isolated nucleic acid as set forth in the Sequence listing as SEQ ID NO: 25. The nucleic acid identified in SEQ ID NO: 25 comprises an 1585 nucleotide open reading frame of the SnSAG3 gene of *Sarcocystis neurona* which encodes a 281 amino acid polypeptide set forth in the Sequence Listing as SEQ ID NO: 26.

Also provided by the present invention is an isolated nucleic acid as set forth in the Sequence listing as SEQ ID NO: 27. The nucleic acid identified in SEQ ID NO: 27 comprises an 1111 nucleotide open reading frame of the SnSAG4 gene of *Sarcocystis neurona* which encodes a 287 amino acid polypeptide set forth in the Sequence Listing as SEQ ID NO: 28.

As set forth more fully below, these genes have been expressed as recombinant proteins in *E. coli*. The recombinant SnSAG proteins can be implemented into antibody-capture ELISAs and used to detect the presence of *S. neurona* antibodies in a sample. Likewise, the recombinant proteins provided by the invention can be used as reagents for use in vaccines against *S. neurona*.

Another embodiment of the present invention includes the discovery of additional novel expressed sequence tags (EST) that encode novel antigenic peptides for utilization in the vaccines and diagnostic kits as disclosed by this invention.

In particular, in a presently preferred embodiment of the invention, cluster analysis of the *Sarcocystis neurona* expressed sequence tags (ESTs) generated from the cSn.1 cDNA library has revealed a gene family that encodes at least eight homologous proteins. Of the approximately 8500 *S. neurona* ESTs that have been generated thus far, roughly 540 sequences can be placed in this gene family, which has been provisionally designated SnGF1 (*S. neurona* Gene Family 1). Based on its relative abundance in the collection of *S. neurona* ESTs, SnGF1 encodes a set of similar proteins (at least eight) that are highly expressed and most likely play significant roles in the biology of *S. neurona* (i.e., parasite virulence factors). In addition to their biological importance, the abundance of these proteins would suggest that they elicit significant immune responses in infected animals. Collectively, the characteristics of the novel nucleic acids of SnGF1, and the encoded proteins therefrom, make this gene family well suited for the development of improved diagnostics and/or vaccines for EPM as set forth herein.

The eight SnGF1 isoforms identified thus far have been designated SnGF1a–h. These genes are predicted to encode proteins of, e.g., 109 amino acids, 106 amino acids, and 107 amino acids in length, and the proteins share approximately 70% to 80% sequence identity. These proteins have a predicted N-terminal signal peptide and a predicted transmembrane domain near the C-terminus. The SnGF1 members show no similarity to sequences in the current public gene databases, suggesting that SnGF1 is relatively unique to *S. neurona*.

Accordingly, one embodiment of the present invention provides an isolated nucleic acid designated SnGF1a which comprises the nucleic acid set forth in SEQ ID NO: 5 and sequences complimentary thereto. Another embodiment of the invention comprises the polypeptide sequence encoded by SnGF1a set forth in the Sequence Listing as SEQ ID NO: 6.

Another embodiment of the present invention provides an isolated nucleic acid designated SnGF1b which comprises the nucleic acid set forth in SEQ ID NO: 7 and sequences complimentary thereto. Another embodiment of the invention comprises the polypeptide sequence encoded by SnGF1b set forth in the Sequence Listing as SEQ ID NO: 8.

Yet another embodiment of the present invention provides an isolated nucleic acid designated SnGF1c which comprises the nucleic acid set forth in SEQ ID NO: 9 and sequences complimentary thereto. Another embodiment of the invention comprises the polypeptide sequence encoded by SnGF1c set forth in the Sequence Listing as SEQ ID NO: 10.

Still another embodiment of the present invention provides an isolated nucleic acid designated SnGF1d which comprises the nucleic acid set forth in SEQ ID NO: 11 and sequences complimentary thereto. Another embodiment of the invention comprises the polypeptide sequence encoded by SnGF1d set forth in the Sequence Listing as SEQ ID NO: 12.

The present invention also provides an isolated nucleic acid designated SnGF1e which comprises the nucleic acid set forth in SEQ ID NO: 13 and sequences complimentary thereto. Another embodiment of the invention comprises the polypeptide sequence encoded by SnGF1e set forth in the Sequence Listing as SEQ ID NO: 14.

Another embodiment of the present invention provides an isolated nucleic acid designated SnGF1f which comprises the nucleic acid set forth in SEQ ID NO: 15 and sequences complimentary thereto. Another embodiment of the invention comprises the polypeptide sequence encoded by SnGF1f set forth in the Sequence Listing as SEQ ID NO: 16.

Yet another embodiment of the present invention provides an isolated nucleic acid designated SnGF1g which comprises the nucleic acid set forth in SEQ ID NO: 17 and sequences complimentary thereto. Another embodiment of the invention comprises the polypeptide sequence encoded by SnGF1g set forth in the Sequence Listing as SEQ ID NO: 18.

Still another embodiment of the present invention provides an isolated nucleic acid designated SnGF1h which comprises the nucleic acid set forth in SEQ ID NO: 19 and sequences complimentary thereto. Another embodiment of the invention comprises the polypeptide sequence encoded by SnGF1h set forth in the Sequence Listing as SEQ ID NO: 20.

The present invention provides isolated nucleic acids as set forth in the Sequence Listing and nucleic acid reagents derived therefrom which can be utilized to diagnose and prevent infection of *S. neurona*. Purified polypeptides encoded by the nucleic acids are also provided. These polypeptides can be utilized in methods of diagnosis or as vaccine components for prevention of infection. Vectors are also provided which comprise the nucleic acids of the present invention. The vectors can be utilized in host expression systems to produce antigenic peptide reagents for diagnostic and prophylactic applications. The present invention also provides purified antibodies selectively reactive with *S. neurona*. These antibodies can be used in various diagnostic methods or as a therapeutic.

In one embodiment, the invention provides purified antigenic polypeptides encoded by the nucleic acids set forth in the Sequence Listing. The invention also provides these antigenic polypeptides in a pharmaceutically acceptable carrier. The amino acid sequence of these polypeptides can be deduced from the nucleotide sequences set forth in the Sequence Listing.

Purified antigenic polypeptide fragments encoded by the nucleic acids of the present invention are also contemplated. As used herein, "purified" means the antigen is at least sufficiently free of contaminants or cell components with which the antigen normally occurs to distinguish the antigen from the contaminants or components. Purified antigenic polypeptides of *S. neurona* and antigenic fragments thereof of the present invention are also referred to herein as "the antigen" or "the *S. neurona* antigen." It is contemplated that the antigenic fragments can be encoded from any portion of the nucleic acid encoding *S. neurona* as set forth in the Sequence Listing, but especially from fragments encoded by the open reading frames set forth in SEQ ID NOS: 24, 26 and 28 as described herein. Specifically, one example provides an approximately 12 kDa antigenic polypeptide encoded by an open reading frame of SEQ ID NO: 24 consisting essentially of the amino acids encoded by the nucleotide as sequence set forth in the Sequence Listing as SEQ ID NO: 23.

An antigenic fragment of the antigen can be isolated from the whole antigen by chemical or mechanical disruption. The purified fragments thus obtained can be tested to determine their antigenicity and specificity by the methods taught herein. Antigenic fragments of the antigen can also be synthesized directly. An immunoreactive fragment is generally an amino acid sequence of at least about five consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of the *S. neurona* antigen attached to sequences designed to provide for some additional property, such as solubility. The amino acid sequences of an *S. neurona* antigen can include sequences in which one or more amino acids have been substituted with another amino acid to provide for some additional property, such as to remove/add amino acids capable of disulfide bonding, to increase its bio-longevity, alter enzymatic activity, or alter interactions, e.g., with gastric acidity. In any case, the peptide should posses a bioactive property, such as immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a horse or a guinea pig, the condition of the subject, the size of the subject, etc. Thereafter an animal so inoculated with the antigen can be exposed to the parasite to test the potential vaccine effect of the specific immunogenic fragment. The specificity of a putative immunogenic fragment can be ascertained by testing sera, other fluids or lymphocytes from the inoculated animal for cross reactivity with other closely related *Sarcocystis* spp.

A vector comprising the nucleic acids of the present invention is also provided. The vectors of the invention can be in a host capable of expressing the antigenic polypeptide fragments contemplated by the present invention. There are numerous *E. coli* expression vectors known to one of ordinary skill in the art useful for the expression of the antigen. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters can be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, for example, an amino terminal methionine can be provided by insertion of a Met codon 5' and in-frame with the antigen. Also, the carboxyterminal extension of the antigenic fragments can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. In one example, the *Saccharomyces cerevisiae* pre-pro-alpha-factor leader region (encoded by the MF.alpha.-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or .beta.-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of a cDNA or opposite strand RNA corresponding to the antigen coding sequence can be confirmed by northern analysis. A number of other suitable host cell lines capable of secreting intact proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other celluar hosts.

Alternative vectors for the expression of antigen in mammalian cells, those similar to those developed for the expression of human gammainterferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

One presently preferred vector system for expression of the peptides of the invention comprises the use of Alphavirus vector constructs, for example, as set forth in U.S. Pat. Nos.: 5,643,576; 5,843,723; 6,156,558; and 6,242,259, the teachings of which are hereby incorporated herein by reference.

A purified monoclonal antibody specifically reactive with S. neurona is also provided. The antibodies can be specifically reactive with a unique epitope of the antigen or they can also react with epitopes of other organisms. The term "reactive" means capable of binding or otherwise associating non randomly with an antigen. "Specifically reactive" as used herein refers to an antibody or other ligand that does not cross react substantially with any antigen other than the one specified, in this case, S. neurona. Antibodies can be made as described in the Examples (see also, Harlow and Lane, Antibodies; A Laboratory Manual, Cold Spring Harbor Laboratory, Cold Spring Harbor, N.Y., 1988). Briefly purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen clone libraries for cells secreting the antigen. Those positive clones can then be sequenced (see, for example, Kelly et al., Bio/Technology, 10: 163–167, (1992) and Bebbington et at., Bio/Technology, 10: 169–175, (1992).

The antibody can be bound to a substrate or labeled with a detectable moiety or both bound and labeled. The detectable moieties contemplated by the present invention include, but are not limited to fluorescent, enzymatic and radioactive markers.

A purified S. neurona antigen bound to a substrate and a ligand specifically reactive with the antigen are also contemplated. Such a purified ligand specifically reactive with the antigen can be an antibody. The antibody can be a monoclonal antibody obtained by standard methods and as described herein. The monoclonal antibody can be secreted by a hybridoma cell line specifically produced for that purpose (Harlow and Lane, 1988). Likewise, nonhuman polyclonal antibodies specifically reactive with the antigen are within the scope of the present invention. The polyclonal antibody can also be obtained by the standard immunization and purification protocols (Harlow and Lane, 1988).

The present invention provides a method of detecting the presence of S. neurona in a subject, comprising the steps of contacting an antibody-containing sample from the subject with a detectable mount of the antigenic polypeptide fragment of the present invention and detecting the reaction of the fragment and the antibody, the reaction indicating the presence of the S. neurona or a previous infection with S. neurona.

One example of the method of detecting S. neurona is performed by contacting a fluid or tissue sample from the subject with an amount of a purified antibody specifically reactive with the antigen as defined herein, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, cerebrospinal fluid, saliva, feces and urine. Other possible examples of body fluids include sputum, mucus, gastric juice and the like.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Another immunologic technique that can be useful in the detection of S. neurona or previous S. neurona infection utilizes monoclonal antibodies (MAbs) for detection of antibodies specifically reactive with S. neurona antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

A micro-agglutination test can also be used to detect the presence of *S. neurona* in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or capable of being detected by a spectrophotometer. In a modification of the above test, antibodies specifically reactive with the antigen can be bound to the beads and antigen in the tissue or body fluid thereby detected.

In addition, as in a typical sandwich assay, the antibody can be bound to a substrate and reacted with the antigen Thereafter, a secondary labeled antibody is bound to epitopes not recognized by the first antibody and the secondary antibody is detected. Since the present invention provides *S. neurona* antigen for the detection of infectious, *S. neurona* or previous *S. neurona* infection other serological methods such as flow cytometry and immunoprecipitation can also be used as detection methods.

In the diagnostic methods taught herein, the antigen can be bound to a substrate and contacted by a fluid sample such as serum, cerebrospinal fluid, urine, saliva, feces or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecific ally with, the ligand or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, 1988).

The antigen, e.g., a purified antigenic polypeptide fragment encoded by the Sequence Listing of this invention can be used in the construction of a vaccine comprising an immunogenic mount of the antigen and a pharmaceutically acceptable carrier. The vaccine can be the entire antigen, the antigen on an intact *S. neurona* organism, *E. coli* or other strain, or an epitope specific to the antigen. The vaccine can also be potentially cross-reactive with antibodies to other antigens. The vaccine can then be used in a method of preventing EPM or other complications of *S. neurona* infection.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier can comprise saline or other suitable carriers (Amon, R. (Ed.) Synthetic Vaccines I: 83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating *S. neurona* infection and the associated diseases by administering the vaccine to a subject.

Nucleic acid vaccines against *S. neurona* are also contemplated by the invention. The antigenic agent for use in the vaccines of the invention can be any nucleic acid, e.g., as set forth in the Sequence Listing, that can stimulate an immune response against, e.g., SnSAG2, SnSAG3 or SnSAG4 when administered to a subject. Suitable nucleic acids include those that encode the native proteins of *S. neurona*, e.g., SnSAG2, SnSAG3 or SnSAG4 protein or a variant or antigenic peptide fragment thereof, such as, e.g., the nucleic acid set forth in the Sequence listing as SEQ ID NO:23, SEQ ID NO:25 or SEQ ID NO:27. The nucleic acid used as a vaccine can be e.g., a naked DNA, or the nucleic acid can be incorporated in an expression vector as set forth herein, e.g., in an Alpha virus vector (see, e.g., Rosenberg, S. A., Immunity 10:281, 1999).

The presence of *S. neurona* can also be determined by detecting the presence of a nucleic acid specific for *S. neurona* or the antigens of *S. neurona* encoded by the nucleic acids set forth herein. The present invention provides a method of detecting the presence of *S. neurona* in a subject, comprising detecting the presence of the nucleic acid encoding *S. neurona*. As set forth more fully in the examples below, the specificity of these sequences for *S. neurona* can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the nucleic acid in question.

The nucleic acid specific for *S. neurona* can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of *S. neurona* comprising ascertaining the presence of a nucleotide sequence associated with a restriction endonuclease cleavage site. In addition, PCR primers which hybridize only with nucleic acids specific for *S. neurona* can be utilized. The presence of amplification indicates the presence of *S. neurona* sequence. In another embodiment a restriction fragment of a nucleic acid sample can be sequenced directly using, techniques known in the art and described herein and compared to the known unique sequence to detect *S. neurona*. In a further embodiment, the present invention provides a method of detecting the presence of *S. neurona* by selective amplification by the methods described herein. In yet another embodiment *S. neurona* can be detected by directly hybridizing the unique sequence with a *S. neurona* selective nucleic acid probe. Furthermore, the nucleotide sequence could be amplified prior to hybridization by the methods described above.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) and reverse transcriptase PCR are techniques that amplify specific nucleic acid sequences with remarkable efficiency. Repeated cycles of denaturation, primer annealing and extension carried out with polymerase; e.g., a heat stable enzyme Taq polymerase, leads to exponential increases in the concentration of desired nucleic acid sequences. Given a knowledge of the nucleotide sequence of *S. neurona* as set forth herein, synthetic oligonucleotides can be prepared which are complementary to sequences which flank the nucleic acid of interest. Each oligonucleotide is complementary to one of the two strands. The nucleic acid can be denatured at high temperatures (e.g., 95.degree. C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template. The end product is then denatured again for another cycle. After this three-step cycle has been repeated several times, amplification of a nucleic acid segment by more than one million-fold can be achieved. The resulting nucleic acid may then be directly sequenced.

In yet another method, PCR may be followed by restriction endonuclease digestion with subsequent analysis of the resultant products. Nucleotide substitutions can result in the gain or loss of specific restriction endonuclease sites. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest.

For RFLP analysis, nucleic acid is obtained, for example from the blood, cerebrospinal fluid, gastric specimen, saliva, dental plaque, other bodily fluids of the subject suspected of containing *S. neurona*, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, *S. neurona* nucleic acid is detected and their mobility on the gel by determining the number of bands detected and comparing this pattern to the nucleic acid from *S. neurona*.

Similar creation of additional restriction sites by nucleotide substitutions at the disclosed mutation sites can be readily calculated by reference to the genetic code and a list of nucleotide sequences recognized by restriction endonucleases. Single strand conformational analysis (SSCA) offers a relatively quick method of detecting sequence changes. which may be appropriate in at least some instances.

In general, primers for PCR and LCR are usually about 20 bp in length and the preferable range is from 15–25 bp. Better amplification is obtained when both primers are the same length and with roughly the same nucleotide composition. Denaturation of strands usually takes place at about 94.degree. C. and extension from the primers is usually at about 72.degree. C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on *S. neurona* isolates or samples obtained from an individual, it can serve as a method of detecting the presence of *S. neurona*. As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

The present invention is more particularly described in the following examples which are intended as illustrative only since numerous modifications and variations therein will be apparent to those skilled in the art.

EXAMPLES

Identification and Characterization of SnSAG1

Surface biotinylation of extracellular merozoites revealed only two dominant labeled molecules that migrate at about 30 kDa and 16 kDa in SDS-PAGE. Analysis of a *S. neurona* EST database (currently 1800+ sequences) identified an orthologue of the 31-kDa surface antigen from *Sarcocystis muris*. The sequence of the *S. neurona* surface antigen gene, designated SnSAG1, is predicted to encode a 276-residue protein with an amino-terminal signal peptide and a carboxy-terminal GPI anchor addition. Antiserum raised against recombinant SnSAG1 recognized a 25-kDa antigen in western blots of non-reduced *S. neurona* lysates, consistent with the molecular weight predicted for the mature SnSAG1. Under reducing conditions, SnSAG1 migrated aberrantly at about 30 kDa, similar to what has been observed in western blot analyses of reduced *T. gondii* surface antigens. Immunofluorescence labeling of SnSAG1 during intracellular growth of *S. neurona* indicated that the protein is expressed throughout schizogony. Interestingly, a filamentous staining pattern was observed in intermediate schizonts that likely reflects localization of the surface antigen to previously-described invaginations of the schizont surface membrane.

Materials and Methods

Parasite Culture

S. neurona strain SN3 [Granstrom, 1992 #1600] merozoites were propagated by serial passage in bovine turbinate (BT) cells and maintained in RPMI 1640 medium supplemented with 10% fetal bovine serum, 2 mM sodium pyruvate, Pen/Strep Fungizone (BioWhittaker, Inc.). Extracellular merozoites were harvested and purified from disrupted host cell monolayers by filtration through 3.0 µm membranes, as described previously for Neaspora caninum [Howe, 1997 #1372].

Immunoscreen of S. neurona cDNA Library

Construction and analyses of the cSn.1 S. neurona merozoite cDNA library has been described previously [Howe, 2001 #1787]. The library was plaqued for 3 hrs at 42° C. on XL 1-Blue MRF' E. coli host cells (Stratagene) grown on 150 mm NZY agar plates. When plaques became visible, plates were overlayed with nitrocellulose filters previously soaked in 10 mM isopropyl-β-D-thiogalactopyranoside (IPTG) for an additional 3 hr incubation at 37° C. Filters were lifted from the plates, washed with TNT buffer (10 mM Tris-HCl, pH 7.5, 150 mM NaCl, 0.05% Tween 20), and blocked in phosphate buffered saline (PBS), 5% dry milk, 5% normal goat serum, 0.05% Tween 20.

Antigenic cDNA clones were identified by screening with cerebrospinal fluid (CSF) from a horse that had been naturally infected with S. neurona and exhibited a high titer of intrathecal antibodies against S. neurona in western blot analysis. Prior to screening the S. neurona cDNA library, the CSF was diluted 1:20 in PBS, 0.1% dry milk, 0.1% normal goat serum, 0.05% Tween 20 and incubated for 30 min with filters carrying plaque lifts of a previously-described N. caninum cDNA library [Howe, 1999 #1759] to remove antibodies that were reactive with E. coli and phage proteins. After adsorption of potential cross-reactive antibodies, the diluted CSF solution was incubated for 1 hr with the cSn.1 filters. After washing, filters were incubated for 1 hr with goat anti-equine IgG conjugated to horseradish peroxidase (HRP) (Jackson Immunoresearch Labs, Inc.) diluted to 1:10,000. Immuno-reactive phage plaques were picked with sterile pipet tips and suspended in 40 µl of SM buffer (50 mM Tris-HCl, pH 7.5, 100 mM NaCl, 8 mM MgSO$_4$, 0.01% gelatin). The cDNA inserts were PCR amplified using the T3 and T7 oligonucleotide primers, and the resulting products were analyzed by agarose gel electrophoresis. Sequencing reactions using T3 primer were conducted on the amplified cDNAs to provide a preliminary identification of the immunoreactive clones. Phagemid excision was performed on selected cDNA clones, and plasmids were rescued in SOLR cells according to the manufacturer's protocol (Stratagene).

S. neurona EST Database Searches and Sequence Analyses

S. neurona homologues to previously-characterized coccidian surface antigens were identified in the S. neurona clustered EST database (See, e.g., paradb.cis.upenn.edu/sarco/index.html) using the BLAST (basic local alignment search tool) set of programs [Altschul, 1990 #616]. At the time the database was searched, it contained 686 consensus sequences that had been generated from 1883 S. neurona ESTs. Selected cDNAs were obtained from the archived collection of EST clones and sequenced using ABI Prism BigDye Terminator Cycle Sequencing reaction mix (Perkin Elmer Applied Biosystems). The reactions were purified using Centri-Sep spin columns (Princeton Separations), and the eluted extension products were resolved and analyzed on an ABI 310 Genetic Analyzer. Sequence analyses were conducted with Genetics Computer Group (GCG) software [Devereux, 1984 #1176] and programs available on the National Center for Biotechnology Information (NCBI) web site (See, e.g., www.ncbi.nlm.nih.gov/) and the Expert Protein Analysis System (ExPASy) server of the Swiss Institute of Bioinformatics (See, e.g., www.expasy.ch/). Multiple sequence alignments were performed using Multalin software [Corpet, 1988 #2046]. The sequence reported herein has been deposited into GenBank under accession number AY032845.

Recombinant SnSAG1 Expression and Generation of Polyclonal Antiserum

The SnSAG1 open reading frame without the predicted amino-terminal signal peptide and the carboxyl-terminal hydrophobic tail was amplified by PCR from the pSnAg8 cDNA using primers that introduce a NdeI restriction site prior to base 45 (numbered from the initiation codon) and an XhoI site after base 743. The amplification product was digested with NdeI and XhoI, ligated into NdeI/XhoI-digested pET22b expression vector (Novagen), and transformed into INVαF' E. coli. The resulting expression plasmid, designated prSnSAG1, was transformed into BL21-CodonPlus E. coli (Stratagene), and a clone that expressed high levels of recombinant SnSAG1 (rSnSAG1) was selected for use. The histidine-tagged rSnSAG1 was purified by nickel-column chromatography according to the manufacturer's protocol (Novagen), and monospecific polyclonal antisera were produced against the purified protein by immunization of a rabbit and rat (Cocalico Biologicals, Inc.).

Western Blot Analysis

Parasites were lysed in sodium dodecyl sulfate (SDS) sample buffer supplemented with protease inhibitor cocktail (Sigma) and 2% 2-mercaptoethanol, and the lysates were separated in 10% or 12% polyacrylamide gels [Laemmli, 1970 #393]. Proteins were transferred to nitrocellulose membranes by semidry electrophoretic transfer in Tris-glycine buffer (pH 8.3). Membranes were blocked with PBS containing 5% nonfat dry milk, 5% goat serum, and 0.05% Tween 20, and then incubated for 1 hr with primary antibody. After washing, membranes were incubated with HRP-conjugated immunoglobulin G secondary antibody (Jackson Immunoresearch Labs, Inc.). Blots were washed, processed for chemiluminescence using Supersignal substrate (Pierce Chemical Company), and exposed to film.

Biotinylation of Surface Proteins and Precipitation with Immobilized Streptavidin Approximately $3 \times 10^7$ freshly harvested merozoites were resuspended in 1 ml cold PBS (pH 7.8). Sulfo-N-hydroxysuccinimide-biotin (Pierce) was added to a concentration of 0.5 mg/ml and incubated at room temperature for 30 min. The labeled parasites were washed twice with 5 ml of PBS and stored at −20° C.

The labeled parasite pellet was lysed with 1 ml radioimmunoprecipitation assay (RIPA) buffer (50 mM Tris [pH 7.5], 1% Triton X-100, 0.5% sodium deoxycholate, 0.2% SDS, 100 mM NaCl, 5 mM EDTA) supplemented with RNase, DNase, protease inhibitor cocktail, and the sample was centrifuged at 16,000×g to remove the insoluble fraction. The soluble proteins were incubated with UltraLink immobilized streptavidin (Pierce), and the precipitated biotin-labeled protein fraction was analyzed by western blotting, as described above.

Immunofluorescent Labeling of Extracellular and Intracellular Parasites

For detection of SnSAG1 on extracellular parasites and in trails deposited by gliding parasites, freshly lysed merozoites were suspended in fresh RPMI 1640 and incubated on poly-L-lysine-coated slides for approximately 30 min. Slides were washed with PBS, and the parasites were fixed in 2.5% formalin-PBS containing 0.01% glutaraldehyde. For detection of SnSAG1 on intracellular parasites, merozoites were inoculated onto BT cells grown on LabTek chamber slides (Nunc). At 24 hr, 48 hr, or 72 hr post-inoculation, the cells were fixed in 2.5% formalin-PBS/0.01% glutaraldehyde and permeablized with 0.2% TritonX-100. After incubation with primary antibody, the slides were rinsed, then incubated with fluorescein isothiocyanate (FITC)-conjugated goat anti-rabbit IgG (Jackson Immunoresearch Labs, Inc.). The slides were mounted in Vectashield with DAPI (Vector Laboratories, Inc.) and examined with a Zeiss axioscope equipped for epifluorescence microscopy.

Results

Isolation and Analysis of Immunoreactive cDNA Clones

A primary screen of the cSn.1 cDNA library identified multiple immunoreactive phage plaques, and a total of 25 plaques were isolated and resuspended in SM buffer. Amplification of the cDNA inserts with T3 and T7 oligonucleotides revealed that 22 of the phage clones had similar lengths of approximately 1500 base pairs (bp), and sequence analysis using T3 primer indicated that these 22 cDNAs represent the same gene. A secondary screen was performed on five of the selected cDNAs, and two highly reactive phage clones, designated SnAgI.8 and SnAgI.9, were chosen for further analyses.

To obtain a preliminary identification of the parasite protein encoded by the selected cDNAs, the SnAgI.9 clone was used to affinity purify antibodies that bind the antigen expressed by this clone, and the eluted antibodies were used to probe a western blot of S. neurona merozoite lysate. As shown in FIG. 1, the purified antibodies reacted with an approximately 31-kDa antigen in reduced S. neurona lysate. Furthermore, the antigen revealed by the phage-purified antibodies comigrated with a protein that is recognized by equine or rabbit antisera against S. neurona as the major immunodominant antigen of this parasite (FIG. 1, lanes 2 and 3). This result implies that the 22 matching cDNA clones isolated during the library screen and represented by SnAgI.8 and SnAgI.9 encode the immunodominant antigen of S. neurona.

Full-length sequence analysis of SnAgI.8 revealed a cDNA insert of 1493 nucleotides, with an open reading frame (ORF) that encodes a 276 amino acid protein. Sequence analysis of SnAgI.9 indicated that this clone was virtually identical to SnAgI.8, although its 3' untranslated region (UTR) was approximately 160 nucleotides longer due to an alternative polyadenylation site. A hydrophobicity plot of the encoded protein showed hydrophobic domains at both termini, which correspond to a predicted signal peptide at the amino terminus and a GPI anchor addition sequence at the carboxyl terminus (data not shown). The signal peptide cleavage is predicted to occur at $Ala^{15}$-$Arg^{16}$ (SignalP; [Nielsen, 1997 #2047], and the most likely GPI transamidase cleavage site is predicted to be at $Ala^{247}$-$Asn^{248}$ (DGPI; Swiss Institute of Bioinformatics). A single N-glycosylation site was predicted at residues 140–143. Removal of the N-terminal and C-terminal signal sequences results in a mature protein of 242 amino acids that has a predicted molecular weight of 24.2 kDa before any potential post-translational modifications (e.g., glycolipid anchor addition, glycosylation).

To identify homology to previously characterized sequences, BLAST searches [Altschul, 1990 #616] of the non-redundant GenBank databases were conducted with the SnAgI.8 coding sequence as the query. These searches revealed a statistically significant similarity to the 31 kDa major surface antigen of Sarcocystis muris [Eschenbacher, 1992 #1767] and a less significant but recognizable similarity to several SAG2-related surface antigens from T. gondii [Lekutis, 2000 #2049]. (FIG. 2). In conjunction with the western blot analysis and the predictions of a signal peptide and a GPI-anchor addition, these results suggested that the gene represented by the SnAgI.8 and SnAgI.9 cDNAs encodes an immunodominant surface antigen of S. neurona; consequently, we tentatively designated this protein SnSAG1, following the genetic nomenclature that is utilized for the related apicomplexan parasites T. gondii and N. caninum [Sibley, 1991 #13; Howe, 1999 #1759].

The sequence analysis for SnGAG2, SnGAG3, and SnGAG4 as well as for the SnGF Cluster sequences provided by the invention and set forth herein have been derived in a fashion similar to that set forth above for SnGAG1. These novel nucleotide sequences and protein sequences of Sarcocystis neurona can be utilized in the production of vaccines and/or antigen/antibody kits for prevention and diagnosis of Sarcocystis neurona infection. One preferred embodiment of the invention is a vaccine comprised of an alpha virus expression vector and nucleic acid selected from the nucleic acid sequences disclosed herein.

Identification of S. neurona Surface Antigens and Expression as Recombinant Proteins Analysis of the S. neurona EST database revealed four paralogous proteins that are homologous to the SAG and SRS surface antigens of Toxoplasma gondii. Each S. neurona gene was predicted to encode a protein that possessed an amino-terminal signal peptide and a carboxyl-terminal glycolipid anchor site, consistent with the proteins being surface antigens. Because of their similarity to Toxoplasma SAGs and their probable surface display on merozoites, the four S. neurona proteins were designated SnSAG1, SnSAG2, SnSAG3, and SnSAG4. The four putative surface antigens were each expressed as a recombinant protein in E. coli, and these were used to immunize rabbits and rats for monospecific polyclonal antisera production. The resulting polyclonal antisera were used in western blot analysis of reduced (with 2-mercaptoethanol) S. neurona lysate to reveal each of the SnSAGs (See, FIG. 3). The mature forms of native SnSAG1 and SnSAG4 are predicted to be approximately 24 kDa, but these antigens co-migrated at approximately 30–32 kDa and correspond to the immunodominant antigen Sn30 that has been described previously (See, FIG. 3) (Granstrom et al., 1993; Liang et al., 1998). SnSAG1 has also been identified by others as a major surface antigen matching the immunodominant Sn30 band (Ellison et al., 2002), but it is apparent that SnSAG4 likely contributes to the antibody reactivity at this molecular weight. The mature form of SnSAG2 is predicted to be about 12 kDa, but this antigen migrated at approximately 18–19 kDa and corresponds to the previously described immunodominant Sn16 antigen (See, FIG. 3) (Granstrom et al., 1993; Liang et al., 1998). Mature SnSAG3 is predicted to be 23 kDa, but migrated at about 28 kDa (See, FIG. 3). The aberrant migration of the SnSAGs under reducing conditions is a characteristic that has been observed previously for the surface antigens of both *T. gondii* (Burg et al., 1988; Cesbron-Delauw et al., 1994) and *N. caninum* (Howe et al., 1998). Importantly, the western blot experiments demonstrated that the recombinant forms of the SnSAGs are recognized by antibodies from *S. neurona*-infected horses. There is strong concordance between antibody recognition of recombinant SnSAG1 (rSnSAG1) and standard western blot analysis of complete parasite antigen (i.e., *S. neurona* merozoite lysate). Similar results were obtained with rSnSAG2, rSnSAG3, and rSnSAG4. These data demonstrate the utility of using the rSnSAGs in ELISA formats to monitor antibody responses in *S. neurona*-infected horses.

Enzyme-Linked Immunosorbent Assays (ELISAs) Based on Recombinant *S. neurona* Surface Antigens (rSnSAGs)

The rSnSAGs expressed in *E. coli* have been shown in western blots to be recognized by equine antibodies; consequently, these recombinant antigens can be utilized as the key reagents for developing ELISAs based on single *S. neurona* antigens. Given the teachings set forth herein and utilizing methods known in the art, an ELISA test can be developed for each of the four rSnSAGs that have been identified by the invention, and all four assays can be optimized and evaluated in detail, as described below.

Expression and Purification of Recombinant SnSAGs.

To produce highly purified recombinant forms of the SnSAGs, the genes for each antigen have been cloned into the pET22b expression plasmid from Novagen (Madison, Wis.). This plasmid vector provides a carboxyl-terminal fusion to a 6-residue oligohistidine domain (His-Tag), which binds to metal ion affinity columns and allows for the efficient one-step purification of the expressed recombinant protein. Plasmid constructs were transformed into BL21 (DE3) host cells (CodonPlus, Stratagene, Inc.), and expression of recombinant protein was induced by addition of IPTG. Bacterial clones that reliably expressed the recombinant SnSAGs were selected and cyropreserved for future study. The recombinant *S. neurona* surface antigens have been designated rSnSAG1, rSnSAG2, rSnSAG3, and rSnSAG4. When recombinant protein is needed for use in the ELISAs, the appropriate bacterial clone can be grown to logarithmic phase in LB medium, and protein expression can be induced by addition of IPTG to the culture. The recombinant protein can be extracted from inclusion bodies with 6 M urea and purified from the host cell lysate by Ni++-column chromatography according to the manufacturer's protocol (His-Bind resin and buffers, Novagen). To remove the urea, purified recombinant proteins can be dialyzed into 350 mM NaCl, 10% glycerol, 50 mM NaH2PO4, 5 mM MgCl2 and stored at −20C until used. If necessary, recombinant proteins can be concentrated by centrifugal ultrafiltration in Centricon-10 columns (Amicon).

Implement the rSnSAGs into ELISA Formats

Standard antibody-capture ELISAs for microtiter plate format can be developed to simplify and expedite serum and CSF testing. For example, recombinant SnSAG1, rSnSAG2, rSnSAG3, or rSnSAG4 can be diluted to 1–10 µg/ml in phosphate-buffered saline (PBS), and 100 µl of the mixture can be added to each well in high-binding capacity ELISA plates (Corning). After overnight incubation at 4C, wells can be blocked by incubation for 1 hr with PBS containing 5% normal goat serum, 0.1% Tween 20, and 0.5% non-fat dry milk. The primary sera or CSF samples can be diluted in PBS/0.1% Tween 20 and incubated in the wells for 2 hrs at room temperature. The wells can then be washed 4 times with PBS/0.1% Tween 20 and incubated with horseradish peroxidase (HRP)-conjugated anti-equine immunoglobulin secondary antibody (Jackson Immunoresearch Labs, Inc.). The wells can again be washed with PBS/Tween, and the presence of bound secondary reagent can be detected by addition of the chromogenic substrate O-phenylenediamine (Sigma-Aldrich) (Harlow and Lane, 1988). The optical density at 490 nm (OD490) of the reactions can be read in an EMax microplate reader (Molecular Devices), and results can be analyzed with SOFTmax PRO 4.0 computer software.

The foregoing descriptions of novel and preferred embodiments of the invention have been presented for purposes of illustration and description. The descriptions are not intended to be exhaustive or to limit the invention to the precise form disclosed. Obvious modifications or variations are possible in light of the above testing. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the claims made in this application when interpreted in accordance with the breadth to which they are fairly, legally and equitably entitled.

References

Alexander, J., T. M. Scharton-Kersten, G. Yap, C. W. Roberts, F. Y. Liew, and A. Sher. 1997. Mechanisms of innate resistance to *Toxoplasma gondii* infection. *Philos Trans R Soc Lond B Biol Sci*. 352:1355–9.

Baszler, T. V., M. T. Long, T. F. McElwain, and B. A. Mathison. 1999. Interferon-gamma and interleukin-12 mediate protection to acute *Neaspora caninum* infection in BALB/c mice. *Int J Parasitol*. 29:1635–46.

Bentz, B. G., D. E. Granstrom, and S. Stamper. 1997. Seroprevalence of antibodies to *Sarcocystis neurona* in horses residing in a county of southeastern Pennsylvania [see comments]. *J Am Vet Med Assoc*. 210:517–8.

Blythe, L. L., D. E. Granstrom, D. E. Hansen, L. L. Walker, J. Bartlett, and S. Stamper. 1997. Seroprevalence of antibodies to *Sarcocystis neurona* in horses residing in Oregon [see comments]. *J Am Vet Med Assoc*. 210:525–7.

Box, E. D., and D. W. Duszynski. 1980. Sarcocystis of passerine birds: sexual stages in the opossum (*Didelphis virginiana*). *J Wildl Dis*. 16:209–15.

Bulow, R., and J. C. Boothroyd. 1991. Protection of mice from fatal Toxoplasma infection by immunization with p30 antigen in liposomes. *Journal of Immunology*. 147: 3496–3500.

Burg, J. L., D. Perlman, L. H. Kasper, P. L. Ware, and J. C. Boothroyd. 1988. Molecular analysis of the gene encoding the major surface antigen of *Toxoplasma gondii*. *J Immunol*. 141:3584–3591.

Cesbron-Delauw, M. F., S. Tomavo, P. Beauchamps, M. P. Fourmaux, D. Camus, A. Capron, and J. F. Dubremetz. 1994. Similarities between the primary structures of two distinct major surface proteins of *Toxoplasma gondii*. *Journal of Biological Chemistry*. 269:16217–16222.

Cheadle, M. A., S. M. Tanhauser, J. B. Dame, D. C. Sellon, M. Hines, P. E. Ginn, R. J. MacKay, and E. C. Greiner. 2001a. The nine-banded armadillo (*Dasypus novemcinctus*) is an intermediate host for *Sarcocystis neurona*. *Int J Parasitol*. 31:330–5.

Cheadle, M. A., C. A. Yowell, D. C. Sellon, M. Hines, P. E. Ginn, A. E. Marsh, J. B. Dame, and E. C. Greiner. 2001b. The striped skunk (*Mephitis mephitis*) is an intermediate host for *Sarcocystis neurona*. *Int J Parasitol*. 31:843–9.

Cutler, T. J., R. J. MacKay, P. E. Ginn, K. Gillis, S. M. Tanhauser, E. V. LeRay, J. B. Dame, and E. C. Greiner. 2001. Immunoconversion against *Sarcocystis neurona* in normal and dexamethasone-treated horses challenged with *S. neurona* sporocysts. *Vet Parasitol*. 95:197–210.

Dubey, J. P., S. W. Davis, C. A. Speer, D. D. Bowman, A. de Lahunta, D. E. Granstrom, M. J. Topper, A. N. Hamir, J. F. Cummings, and M. M. Suter. 1991. *Sarcocystis neurona* n. sp. (Protozoa: Apicomplexa), the etiologic agent of equine protozoal myeloencephalitis. *J Parasitol*. 77:212–8.

Dubey, J. P., D. S. Lindsay, O. C. Kwok, and S. K. Shen. 2001a. The gamma interferon knockout mouse model for *sarcocystis neurona*: comparison of infectivity of sporocysts and merozoites and routes of inoculation. *J Parasitol*. 87:1171–3.

Dubey, J. P., D. S. Lindsay, W. J. Saville, S. M. Reed, D. E. Granstrom, and C. A. Speer. 2001b. A review of *Sarcocystis neurona* and equine protozoal myeloencephalitis (EPM). *Vet Parasitol*. 95:89–131.

Dubey, J. P., W. J. Saville, D. S. Lindsay, R. W. Stich, J. F. Stanek, C. A. Speert, B. M. Rosenthal, C. J. Njoku, O. C. Kwok, S. K. Shen, and S. M. Reed. 2000. Completion of the life cycle of *Sarcocystis neurona*. *J Parasitol*. 86:1276–80.

Dubey, J. P., W. J. Saville, J. F. Stanek, D. S. Lindsay, B. M. Rosenthal, M. J. Oglesbee, A. C. Rosypal, C. J. Njoku, R. W. Stich, O. C. Kwok, S. K. Shen, A. N. Hamir, and S. M. Reed. 2001c. *Sarcocystis neurona* infections in raccoons (*Procyon lotor*): evidence for natural infection with sarcocysts, transmission of infection to opossums (*Didelphis virginiana*), and experimental induction of neurologic disease in raccoons. *Vet Parasitol*. 100:117–29.

Dubey, J. P., R. H. Streitel, P. C. Stromberg, and M. J. Toussant. 1977. *Sarcocystis fayeri* sp. n. from the horse. *J Parasitol*. 63:443–7.

Dzierszinski, F., M. Mortuaire, M. F. Cesbron-Delauw, and S. Tomavo. 2000. Targeted disruption of the glycosylphosphatidylinositol-anchored surface antigen SAG3 gene in *Toxoplasma gondii* decreases host cell adhesion and drastically reduces virulence in mice. *Mol Microbiol*. 37:574–82.

Ellison, S. P., A. L. Omara-Opyene, C. A. Yowell, A. E. Marsh, and J. B. Dame. 2002. Molecular characterisation of a major 29 kDa surface antigen of *Sarcocystis neurona*. *Int J Parasitol*. 32:217–25.

Fenger, C. K., D. E. Granstrom, A. A. Gajadhar, N. M. Williams, S. A. McCrillis, S. Stamper, J. L. Langemeier, and J. P. Dubey. 1997. Experimental induction of equine protozoal myeloencephalitis in horses using *Sarcocystis* sp. sporocysts from the opossum (*Didelphis virginiana*). *Vet Parasitol*. 68:199–213.

Fenger, C. K., D. E. Granstrom, J. L. Langemeier, A. Gajadhar, G. Cothran, R. R. Tramontin, S. Stamper, and J. P. Dubey. 1994. Phylogenetic relationship of *Sarcocystis neurona* to other members of the family Sarcocystidae based on small subunit ribosomal RNA gene sequence. *J Parasitol*. 80:966–75.

Fenger, C. K., D. E. Granstrom, J. L. Langemeier, S. Stamper, J. M. Donahue, J. S. Patterson, A. A. Gajadhar, J. V. Marteniuk, Z. Xiaomin, and J. P. Dubey. 1995. Identification of opossums (*Didelphis virginiana*) as the putative definitive host of *Sarcocystis neurona*. *J Parasitol*. 81:916–9.

Finkelman, F. D., J. Holmes, I. M. Katona, J. F. Urban, Jr., M. P. Beckmann, L. S. Park, K. A. Schooley, R. L. Coffman, T. R. Mosmann, and W. E. Paul. 1990. Lymphokine control of in vivo immunoglobulin isotype selection. *Annu Rev Immunol*. 8:303–33.

Granstrom, D. E., J. P. Dubey, S. W. Davis, R. Fayer, J. C. Fox, K. B. Poonacha, R. C. Giles, and P. F. Comer. 1993. Equine protozoal myeloencephalitis: antigen analysis of cultured *Sarcocystis neurona* merozoites. *J Vet Diagn Invest*. 5:88–90.

Grimwood, J., and J. E. Smith. 1992. *Toxoplasma gondii*: The role of a 30-kDa surface protein in host cell invasion. *Experimental Parasitology*. 74:106–111.

Handman, E., and J. S. Remington. 1980. Antibody responses to Toxoplasma antigens in mice infected with strains of different virulence. *Infection Immunity*. 29:215–220.

Harlow, E., and D. Lane. 1988. Antibodies: A laboratory manual. Cold Spring Harbor Laboratory, Cold Spring Harbor, N.Y. 726 pp. He, X. L., M. E. Grigg, J. C. Boothroyd, and K. C.

Garcia. 2002. Structure of the immunodominant surface antigen from the *Toxoplasma gondii* SRS superfamily. *Nat Struct Biol*. 9:606–11.

Hemphill, A. 1996. Subcellular localization and functional characterization of Nc-p43. *Infection and Immunity*. 64:4279–4287.

Howe, D. K. 2001. Initiation of a *Sarcocystis neurona* expressed sequence tag (EST) sequencing project: a preliminary report. *Vet Parasitol*. 95:233–9.

Howe, D. K., A. C. Crawford, D. Lindsay, and L. D. Sibley. 1998. The p29 and p35 immunodominant antigens of *Neaspora caninum* tachyzoites are homologous to the family of surface antigens of *Toxoplasma gondii*. *Infection and Immunity*. 66:5322–5328.

Howe, D. K., and L. D. Sibley. 1999. Comparison of the major antigens of *Neaspora caninum* and *Toxoplasma gondii*. *Int J Parasitol*. 29:1489–96.

Howe, D. K., K. Tang, P. A. Conrad, K. Sverlow, J. P. Dubey, and L. D. Sibley. 2002. Sensitive and specific identification of *Neaspora caninum* infection of cattle based on detection of serum antibodies to recombinant Ncp29. *Clin Diagn Lab Immunol*. 9:611–5.

Jacquet, A., L. Coulon, J. De Neve, V. Daminet, M. Haumont, L. Garcia, A. Bollen, M. Jurado, and R. Biemans. 2001. The surface antigen SAG3 mediates the attachment of *Toxoplasma gondii* to cell-surface proteoglycans. *Mol Biochem Parasitol*. 116:35–44.

Krahenbuhl, J. L., and J. S. Remington. 1982. The immunology of Toxoplasma and toxoplasmosis. In Immunology of Parasitic Infections. S. Cohen and K. S. Warren, editors. Blackwell Scientific Publications. 356–421.

Lekutis, C., D. J. Ferguson, M. E. Grigg, M. Camps, and J. C. Boothroyd. 2001. Surface antigens of *Toxoplasma gondii*: variations on a theme. *Int J Parasitol*. 31:1285–92.

Liang, F. T., D. E. Granstrom, X. M. Zhao, and J. F. Timoney. 1998. Evidence that surface proteins Sn14 and Sn16 of *Sarcocystis neurona* merozoites are involved in infection and immunity. *Infect Immun.* 66:1834–8.

MacKay, R. J., D. E. Granstrom, W. J. Saville, and S. M. Reed. 2000. Equine protozoal myeloencephalitis. *Vet Clin North Am Equine Pract.* 16:405–25.

Marsh, A. E., B. C. Barr, J. Lakritz, R. Nordhausen, J. E. Madigan, and P. A. Conrad. 1997. Experimental infection of nude mice as a model for *Sarcocystis neurona*-associated encephalitis. *Parasitol Res.* 83:706–11.

Marsh, A. E., B. C. Barr, J. Madigan, J. Lakritz, and P. A. Conrad. 1996. Sequence analysis and polymerase chain reaction amplification of small subunit ribosomal DNA from *Sarcocystis neurona*. *Am J Vet Res.* 57:975–81.

Miller, M. M., C. R. Sweeney, G. E. Russell, R. M. Sheetz, and J. K. Morrow. 1999. Effects of blood contamination of cerebrospinal fluid on western blot analysis for detection of antibodies against *Sarcocystis neurona* and on albumin quotient and immunoglobulin G index in horses. *J Am Vet Med Assoc.* 215:67–71.

Mineo, J. R., and L. H. Kasper. 1994. Attachment of *Toxoplasma gondii* to host cells involves major surface protein SAG-1 (P30). *Experimental Parasitology.* 79:11–20.

Mineo, J. R., R. McLeod, D. Mack, J. Smith, I. A. Khan, K. H. Ely, and L. H. Kasper. 1993. Antibodies to *Toxoplasma gondii* major surface protein (SAG-1, P30) inhibit infection of host cells and are produced in murine intestine after peroral infection. *The Journal of Immunology.* 150: 3951–3964.

Rooney, J. R., M. E. Prickett, F. M. Delaney, and M. W. Crowe. 1970. Focal myelitis-encephalitis in horses. *Cornell Vet.* 60:494–501.

Rossano, M. G., L. S. Mansfield, J. B. Kaneene, A. J. Murphy, C. M. Brown, H. C. Schott, 2nd, and J. C. Fox. 2000. Improvement of western blot test specificity for detecting equine serum antibodies to *Sarcocystis neurona*. *J Vet Diagn Invest.* 12:28–32.

Saville, W. J., S. M. Reed, D. E. Granstrom, K. W. Hinchcliff, C. W. Kohn, T. E. Wittum, and S. Stamper. 1997. Seroprevalence of antibodies to *Sarcocystis neurona* in horses residing in Ohio [see comments]. *J Am Vet Med Assoc.* 210:519–24.

Saville, W. J., R. W. Stich, S. M. Reed, C. J. Njoku, M. J. Oglesbee, A. Wunschmann, D. L. Grover, A. L. Larew-Naugle, J. F. Stanek, D. E. Granstrom, and J. P. Dubey. 2001. Utilization of stress in the development of an equine model for equine protozoal myeloencephalitis. *Vet Parasitol.* 95:211–22.

Sharma, S. D., J. Mullenax, F. G. Araujo, H. A. Ehrlich, and J. S. Remington. 1983. Western blot analysis of the antigens of *Toxoplasma gondii* recognized by human IgM and IgG antibodies. *Journal of Immunology.* 131:977–983.

Smith, R. D. 1991. Veterinary Clinical Epidemiology: A Problem-Oriented Approach. Butterworth-Heinemann, Boston, Mass. 234 pp.

Snapper, C. M., K. B. Marcu, and P. Zelazowski. 1997. The immunoglobulin class switch: beyond "accessibility". *Immunity.* 6:217–23.

What is claimed is:

1. A composition comprising an isolated nucleic acid comprising a sequence set forth in the Sequence Listing as SEQ ID NO: 23 and sequences fully complementary thereto.

2. A vector comprising the nucleic acid of claim 1.

3. The vector of claim 2 in a host that expresses the polypeptide encoded by the nucleic acid.

4. The vector of claim 2, wherein the vector is selected from the group consisting of a E. Coli bacteria and an Alpha virus.

5. The composition of claim 1, wherein the isolated nucleic acid is capable of hybridizing under stringent conditions with a nucleic acid from Sarcocystis neurona.

6. The composition of claim 1, further comprising a pharmaceutically acceptable carrier.

7. A composition comprising an isolated nucleic acid capable of encoding an antigenic protein derived from Sarcocystis neurona or an antigenic polypeptide fragment thereof comprising a nucleotide sequence set forth in the Sequence Listing as SEQ ID NO: 23 and sequences fully complementary thereto.

8. A vector comprising the nucleic acid of claim 7.

9. The vector of claim 8 in a host that expresses the polypeptide encoded by the nucleic acid.

10. The vector of claim 8, wherein the vector is selected from the group consisting of a E. Coli bacteria and an Alpha virus.

11. The composition of claim 1, wherein the isolated nucleic acid is capable of hybridizing under conditions of low stringency with a nucleic acid from Sarcocystis neurona.

12. The composition of claim 1, wherein the isolated nucleic acid is capable of hybridizing under conditions of moderate stringency with a nucleic acid from Sarcocystis neurona.

13. The composition of claim 1, wherein the isolated nucleic acid is capable of hybridizing under conditions of high stringency with a nucleic acid from Sarcocystis neurona.

14. An isolated nucleic acid sequence comprising the nucleotide sequence of SEQ ID NO.: 23, or a degenerate variant thereof, that encodes a polypeptide comprising the amino acid sequence of SEQ ID NO.: 24.

15. A vector comprising the nucleic acid of claim 14.

16. The vector of claim 14 in a host that expresses the polypeptide encoded by the nucleic acid.

* * * * *